(12) United States Patent
McClurken et al.

(10) Patent No.: US 8,348,946 B2
(45) Date of Patent: Jan. 8, 2013

(54) SURGICAL DEVICES AND METHODS OF USE THEREOF

(75) Inventors: Michael E. McClurken, Durham, NH (US); Roger D. Greeley, Portsmouth, NH (US); Brian M. Conley, South Berwick, ME (US)

(73) Assignee: Medtronic Advanced Energy LLC, Minneapolis, MN (US)

( * ) Notice: Subject to any disclaimer, the term of this patent is extended or adjusted under 35 U.S.C. 154(b) by 0 days.

(21) Appl. No.: 13/494,574

(22) Filed: Jun. 12, 2012

(65) Prior Publication Data

US 2012/0253343 A1    Oct. 4, 2012

Related U.S. Application Data

(62) Division of application No. 12/053,030, filed on Mar. 21, 2008, now Pat. No. 8,216,233.

(60) Provisional application No. 60/896,768, filed on Mar. 23, 2007.

(51) Int. Cl.
    *A61B 18/14* (2006.01)
(52) U.S. Cl. .......................................... 606/50; 606/40
(58) Field of Classification Search .............. 606/21–31, 606/41, 48–50
    See application file for complete search history.

(56) References Cited

U.S. PATENT DOCUMENTS

| 4,936,281 A | 6/1990 | Stasz |
| 5,098,431 A | 3/1992 | Rydell |
| 5,383,876 A | 1/1995 | Nardella |
| 5,395,363 A | 3/1995 | Billings et al. |
| 5,460,629 A | 10/1995 | Shlain et al. |
| 5,484,435 A | 1/1996 | Fleenor et al. |
| 6,004,269 A | 12/1999 | Crowley et al. |
| 6,053,937 A | 4/2000 | Edwards et al. |
| 6,149,646 A | 11/2000 | West, Jr. et al. |
| 6,485,490 B2 | 11/2002 | Wampler et al. |

(Continued)

FOREIGN PATENT DOCUMENTS

JP            2003079633         3/2003

(Continued)

OTHER PUBLICATIONS

Salameh et al. "An Animal Tissue Model Study to Clarify and Investigate Endoscopic Tissue Coagulation by Using a New Monopolar Device," Gastrointestinal Endoscopy, Jan. 2004, vol. 59, No. 1, p. 107-112.

(Continued)

*Primary Examiner* — Lee S Cohen
*Assistant Examiner* — Khadijeh Vahdat
(74) *Attorney, Agent, or Firm* — Sterne, Kessler, Goldstein & Fox P.L.L.C.

(57) ABSTRACT

The invention provides surgical devices and methods to treat tissue. In one device embodiment, the invention comprises a bipolar electrosurgical device to treat tissue in a presence of radio frequency power and a fluid provided simultaneously from a distal portion of the device, with the device comprising a disc shaped distal end. In one method embodiment, the invention comprises a method of treating tissue having a blood vessel during spine surgery, with the method comprising pressing a portion of the blood vessel against a supporting spine structure with a surgical device to provide a compressed portion of the blood vessel, and heating the compressed portion of the blood vessel with the surgical device sufficiently to inhibit a blood flow through the vessel after the surgical device is removed from the blood vessel.

16 Claims, 15 Drawing Sheets

U.S. PATENT DOCUMENTS

| | | | |
|---|---|---|---|
| 6,575,968 B1 | 6/2003 | Eggers et al. | |
| 6,602,242 B1 | 8/2003 | Fung et al. | |
| 6,656,174 B1 | 12/2003 | Hedge et al. | |
| 6,702,810 B2 | 3/2004 | McClurken et al. | |
| 6,960,200 B2 | 11/2005 | Shapeton et al. | |
| 6,979,328 B2 | 12/2005 | Baerveldt et al. | |
| 7,104,990 B2 | 9/2006 | Jenkins et al. | |
| 7,112,199 B2 | 9/2006 | Cosmescu | |
| 7,147,637 B2 | 12/2006 | Goble | |
| 7,175,644 B2 | 2/2007 | Cooper et al. | |
| 7,455,669 B2 | 11/2008 | Swanson | |
| 7,571,729 B2 | 8/2009 | Saadat et al. | |
| 7,621,910 B2 | 11/2009 | Sugi | |
| 7,811,282 B2 | 10/2010 | McClurken | |
| 7,819,861 B2 | 10/2010 | Auge, II et al. | |
| 7,819,864 B2 | 10/2010 | Morgan et al. | |
| 2001/0001314 A1 | 5/2001 | Davison et al. | |
| 2001/0014806 A1 | 8/2001 | Ellman et al. | |
| 2002/0049438 A1 | 4/2002 | Sharkey et al. | |
| 2002/0077626 A1 | 6/2002 | Ellman et al. | |
| 2002/0198520 A1 | 12/2002 | Coen et al. | |
| 2003/0233023 A1* | 12/2003 | Khaghani et al. | 600/18 |
| 2004/0243121 A1 | 12/2004 | Lee et al. | |
| 2005/0059966 A1 | 3/2005 | McClurken et al. | |
| 2005/0070894 A1 | 3/2005 | McClurken | |
| 2005/0090816 A1 | 4/2005 | McClurken et al. | |
| 2005/0154386 A1 | 7/2005 | West et al. | |
| 2005/0288665 A1 | 12/2005 | Woloszko | |
| 2006/0052776 A1 | 3/2006 | Desinger et al. | |
| 2006/0106375 A1 | 5/2006 | Werneth et al. | |
| 2006/0149225 A1 | 7/2006 | McClurken | |
| 2007/0027449 A1 | 2/2007 | Godara et al. | |
| 2007/0270791 A1 | 11/2007 | Wang et al. | |
| 2008/0033421 A1 | 2/2008 | Davis et al. | |
| 2008/0221567 A1 | 9/2008 | Sixto et al. | |
| 2009/0118732 A1 | 5/2009 | Desinger | |
| 2009/0156981 A1 | 6/2009 | Fay et al. | |
| 2009/0177192 A1 | 7/2009 | Rioux et al. | |
| 2009/0270856 A1 | 10/2009 | Saadat et al. | |
| 2010/0036371 A1 | 2/2010 | Park et al. | |
| 2010/0100095 A1 | 4/2010 | McClurken et al. | |
| 2010/0114095 A1 | 5/2010 | Janssen et al. | |
| 2010/0160906 A1 | 6/2010 | Jarrard | |
| 2010/0204560 A1 | 8/2010 | Salahieh et al. | |
| 2010/0241178 A1 | 9/2010 | Tilson et al. | |
| 2010/0312259 A1 | 12/2010 | Houser et al. | |
| 2010/0331883 A1 | 12/2010 | Schmitz et al. | |

FOREIGN PATENT DOCUMENTS

| | | | |
|---|---|---|---|
| SU | 1161093 A | * | 6/1985 |
| WO | WO-02060523 | | 8/2002 |

OTHER PUBLICATIONS

Palanker et al. "Electrosurgery with Cellular Precision," IEEE Transactions on Biomedical Engineering, Feb. 2008. vol. 55, No. 2, p. 838-841.

McCauley, Genard, "Understanding Electrosurgery," MC-55-049-001 Rev.2, 2010, 16 pages, Bovie Medical Corporation Clearwater, FL, United States.

International Search Report and Written Opinion dated Aug. 29, 2008, issued in related International Patent Appln No. PCT/US08/057815.

European Search Report dated Mar. 1, 2010, issued in related European Patent Appln No. 08744175.4-2305.

* cited by examiner

SURGICAL DEVICES AND METHODS OF USE THEREOF

CROSS REFERENCE TO RELATED APPLICATIONS

The present application is a divisional of U.S. application Ser. No. 12/053,030, filed Mar. 21, 2008, now U.S. Pat. No. 8,216,233 issued Jul. 10, 2012, which claims the benefit of the filing date of U.S. Provisional Application Ser. No. 60/896,768, filed Mar. 23, 2007. The teachings of each of these applications are incorporated herein by reference.

FIELD

This invention relates to surgical devices, systems and methods for use upon tissues of a human body during surgery, particularly open surgery and minimally invasive surgery such as laparoscopic surgery.

BACKGROUND

A dry tip electrosurgical device, such as a Bovie pencil, can cause the temperature of tissue being treated to rise significantly higher than 100° Celsius, resulting in tissue desiccation, tissue sticking to the electrodes, tissue perforation, char formation and smoke generation.

Furthermore, certain surgical devices are too large to be used in confined surgical spaces and/or are simply ineffective in treating tissue, such as to inhibit blood loss.

More recently, fluid-assisted electrosurgical devices have been developed which use saline to inhibit undesirable effects such as tissue desiccation, electrode sticking, smoke production and char formation during the treatment of tissue. However, too much saline can provide too much electrical dispersion and cooling at the electrode-tissue interface. This reduces the temperature of the tissue being treated and, in turn, can result in a longer treatment time to achieve the desired tissue temperature for treatment of the tissue. Long treatment times are undesirable for surgeons since it is in the best interest of the patient, physician and hospital to perform surgical procedures as quickly as possible.

In light of the above, there is a need for devices and methods which address the foregoing concerns.

SUMMARY OF THE INVENTION

The invention, in one embodiment, provides an electrosurgical apparatus to provide controlled delivery of radio-frequency power and a fluid to an electrosurgical hand held device to treat tissue. The apparatus comprises a radio-frequency generator to deliver the radio-frequency power, with the radio frequency power from the radio-frequency generator selectable at a radio-frequency power level; a pump to deliver the fluid; a primer to prime the hand device with the fluid; a control system to control a flow of the fluid delivered by the pump with a functional relationship between the radio-frequency power level and the flow of the fluid, the functional relationship to increase the flow of the fluid in response to an increase in the radio-frequency power level and to decrease the flow of the fluid in response to a decrease in the radio-frequency power level; and a fluid flow selector which changes the functional relationship between the radio-frequency power level and the flow of the fluid.

In another embodiment, the invention provides a bipolar electrosurgical device to treat tissue. The device comprises a handle and a shaft extending distally from the handle with the shaft supporting the distal portion of the device in rigid relation to the handle. The distal portion of the device terminates at a distal end comprising a disc shaped distal end. The disc shaped distal end comprises a first semi-circular shaped electrode and a second semi-circular shaped electrode. The device may further comprise a fluid delivery passage being connectable to a fluid source of fluid and at least one fluid exit in fluid communication with the fluid delivery passage.

In another embodiment, the invention provides a method of treating tissue having a blood vessel during spine surgery with the method comprising pressing a portion of the blood vessel against a supporting spine structure with a surgical device to provide a compressed portion of the blood vessel, and heating the compressed portion of the blood vessel with the surgical device sufficiently to occlude the blood vessel after the surgical device is removed from the blood vessel. In certain embodiments, the supporting spine structure comprises a vertebra, and more particularly, a vertebral body of the vertebra.

In another embodiment, the invention provides a method of treating tissue having a blood vessel during surgery with the method comprising pressing a portion of the blood vessel against a bone structure with a surgical device to provide a compressed portion of the blood vessel, and heating the compressed portion of the blood vessel with the surgical device sufficiently to occlude the blood vessel after the surgical device is removed from the blood vessel.

In another embodiment, the invention provides an electrically powered surgical device to be used during a surgical procedure with the device comprising an aperture formed in the device; the aperture having a button therein to activate the device, the aperture defined by a perimeter wall surrounding the button; a narrow gap between the button and the perimeter wall, the narrow gap open to a flow of fluid therein from the surgical procedure, the fluid comprising blood; and the button having at least one side closely adjacent the perimeter wall surrounding the button, the at least one side of the button having at least one aperture formed therein to inhibit the button from adhering with the perimeter wall by the blood.

It is understood that the specific features described in these embodiments can be rearranged among the various embodiments to provide devices, apparatus, systems and methods that fall within the scope of this disclosure.

DETAILED DESCRIPTION

Figure 1:
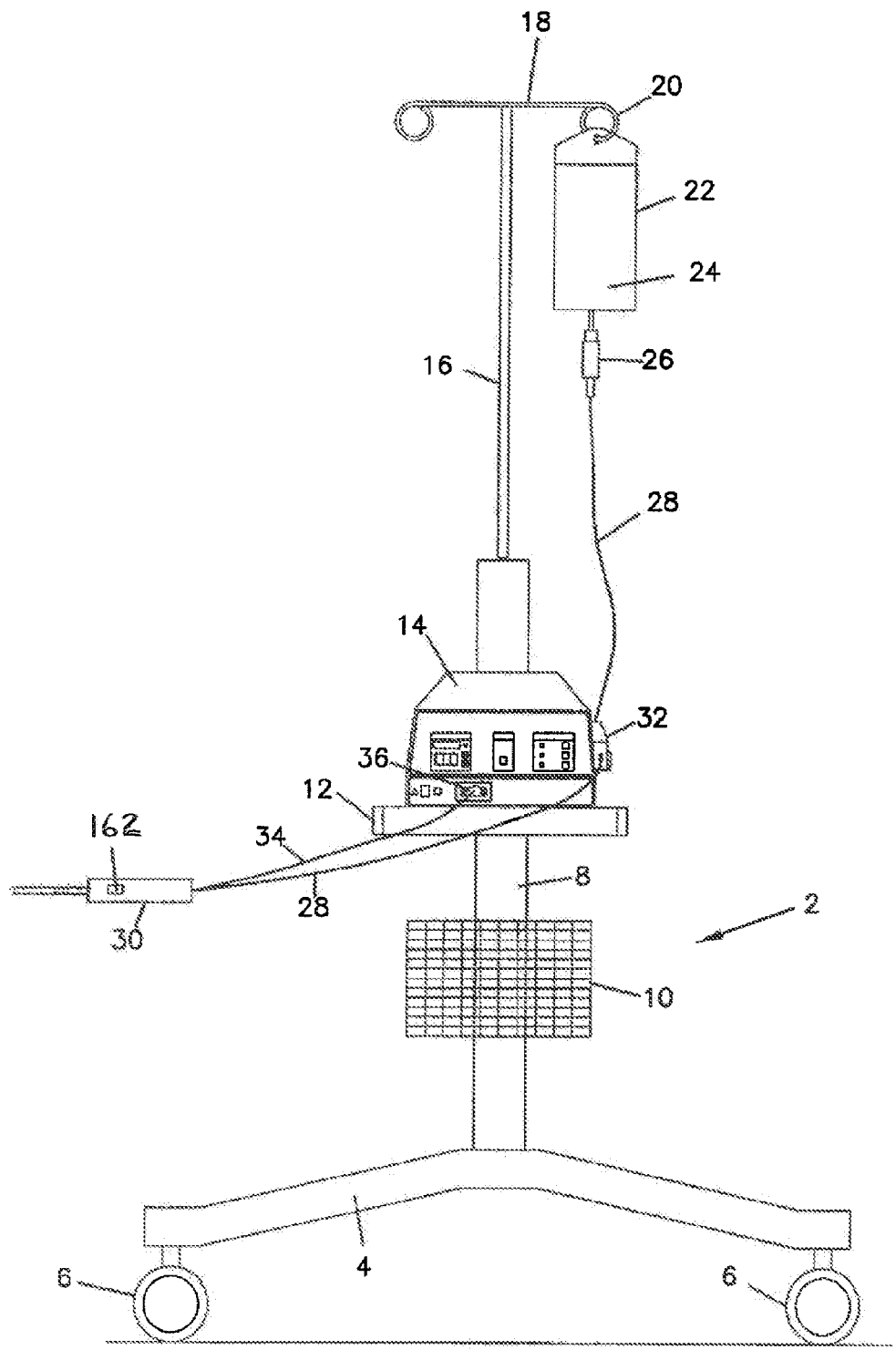
FIG. 1 is a front view of one embodiment of a system of the present invention having an electrosurgical unit in combination with a fluid source and handheld electrosurgical device.

Throughout the description, like reference numerals and letters indicate corresponding structure throughout the several views. Also, any particular feature(s) of a particular exemplary embodiment may be equally applied to any other exemplary embodiment(s) of this specification as suitable. In other words, features between the various exemplary embodiments described herein are interchangeable as suitable, and not exclusive. From the specification, it should be clear that any use of the terms "distal" and "proximal" are made in reference from the user of the device, and not the patient.

The inventions disclosed herein provide devices, systems and methods for treating tissue during a surgical procedure. These inventions are particularly useful for procedures where it is desirable to shrink, coagulate and seal tissue against blood loss, for example, by shrinking lumens of blood vessels (e.g., veins, arteries).

The invention will now be discussed with reference to the figures, with FIG. 1 showing a front view of one embodiment of a system of the present invention having an electrosurgical unit 14 in combination with a fluid source 22 and a handheld electrosurgical device 30. FIG. 1 shows a movable cart 2 having a chassis 4 which is provided with four wheels 6 for easy transportation. The chassis 4 carries a vertical support member 8 comprising a hollow cylindrical post to which a storage basket 10 may be fastened and used to store the electrosurgical unit's user manual, as well as additional unused devices. Furthermore, the support member 8 carries a platform 12 comprising a pedestal table to provide a flat, stable surface for location of the electrosurgical unit 14.

As shown, cart 2 further comprises a fluid source carrying pole 16 having a height which may be adjusted by sliding the carrying pole 16 up and down within the support member 8 and thereafter secured in position with a set screw. On the top of the fluid source carrying pole 16 is a cross support 18 provided with loops 20 at the ends thereof to provide a hook for carrying fluid source 22.

Returning to FIG. 1, fluid source 22 comprises a bag of fluid from which the fluid 24 flows through a drip chamber 26 after the bag is penetrated with a spike located at the end of the drip chamber 26. Thereafter, fluid 24 flows through flexible delivery tubing 28 to handheld electrosurgical device 30. Preferably the fluid delivery tubing 28 is made from a polymer material.

Figure 6:
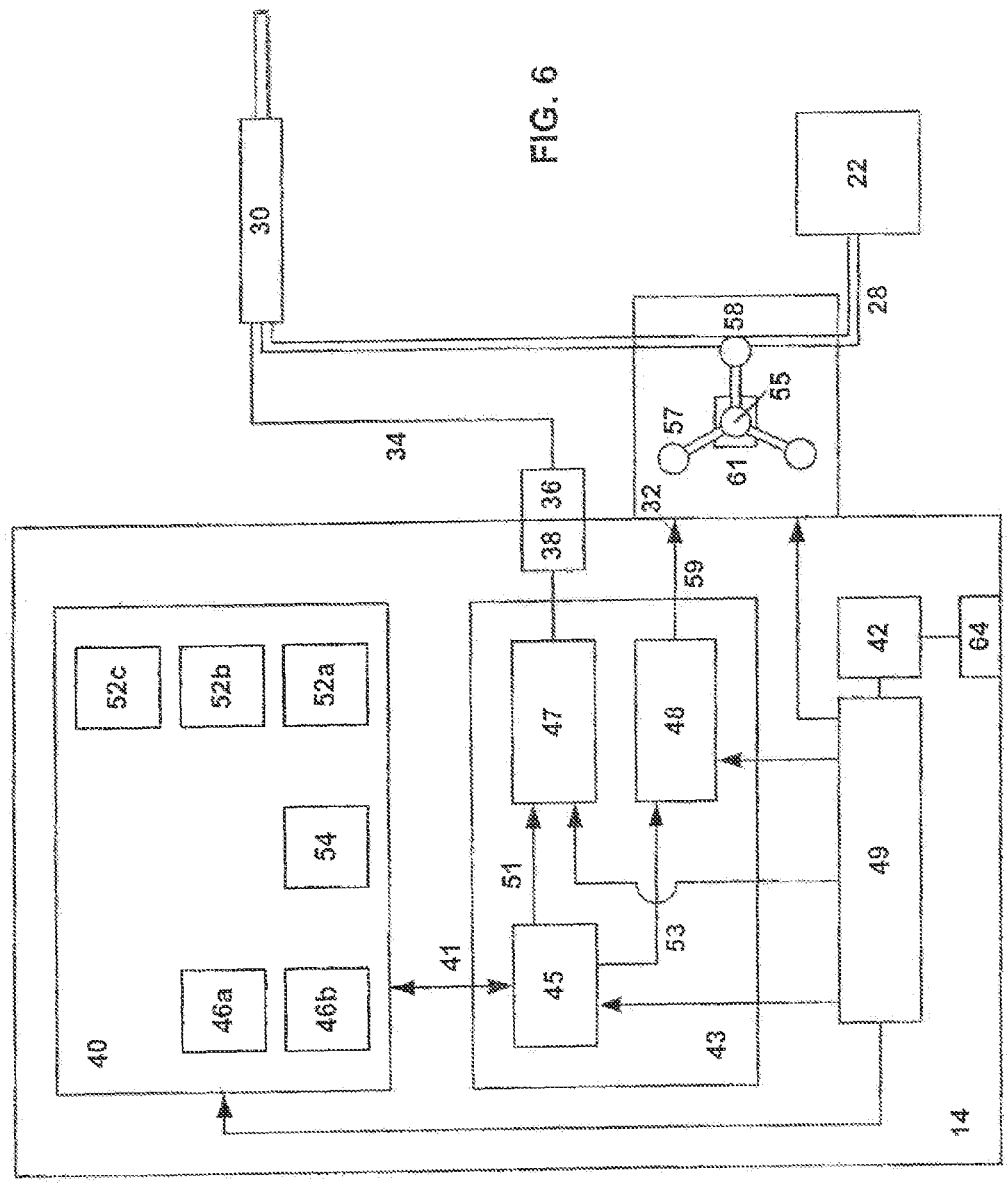
FIG. 6 is a block diagram showing one embodiment of how the electrosurgical unit processes the inputs of RF power setting $P_S$ and the fluid flow rate setting, either $Q_L$, $Q_M$ or $Q_H$, to control the pump speed.

As shown in FIG. 1, the fluid delivery tubing 28 passes through pump 32. As shown pump 32 comprises a peristaltic pump and, more specifically, a rotary peristaltic pump. With a rotary peristaltic pump, a portion of the delivery tubing 28 is loaded into the pump head by raising and lowering the pump head in a known manner. As best shown in FIG. 6, fluid 24 is conveyed within the delivery tubing 28 by waves of contraction placed externally on the tubing 28 which are produced mechanically, typically by rotating pinch rollers 57 which rotate on a drive shaft 55 and intermittently compress the tubing 28 against an anvil support 58. Alternatively, pump 32 may comprise a linear peristaltic pump. With a linear peristaltic pump, fluid 24 is conveyed within the delivery tubing 28 by waves of contraction placed externally on the tubing 28 which are produced mechanically, typically by a series of compression fingers or pads which sequentially squeeze the tubing 28 against a support. Peristaltic pumps are generally preferred, as the electro-mechanical force mechanism, here rollers driven by electric motor, does not make contact the fluid 24, thus reducing the likelihood of inadvertent contamination.

In a preferred embodiment the fluid 24 comprises saline, and even more preferably, normal (physiologic) saline. Although the description herein may make reference to saline as the fluid 24, other electrically conductive fluids can be used in accordance with the invention.

While a conductive fluid is preferred, as will become more apparent with further reading of this specification, fluid 24 may also comprise an electrically non-conductive fluid. The use of a non-conductive fluid is less preferred than a conductive fluid, however, the use of a non-conductive fluid still provides certain advantages over complete elimination of the fluid and the use of a dry electrode including, for example, reduced occurrence of tissue sticking to the electrode of device 30 and cooling of the electrode and/or tissue. Therefore, it is also within the scope of the invention to include the use of a non-conducting fluid, such as, for example, deionized water.

Figure 2:
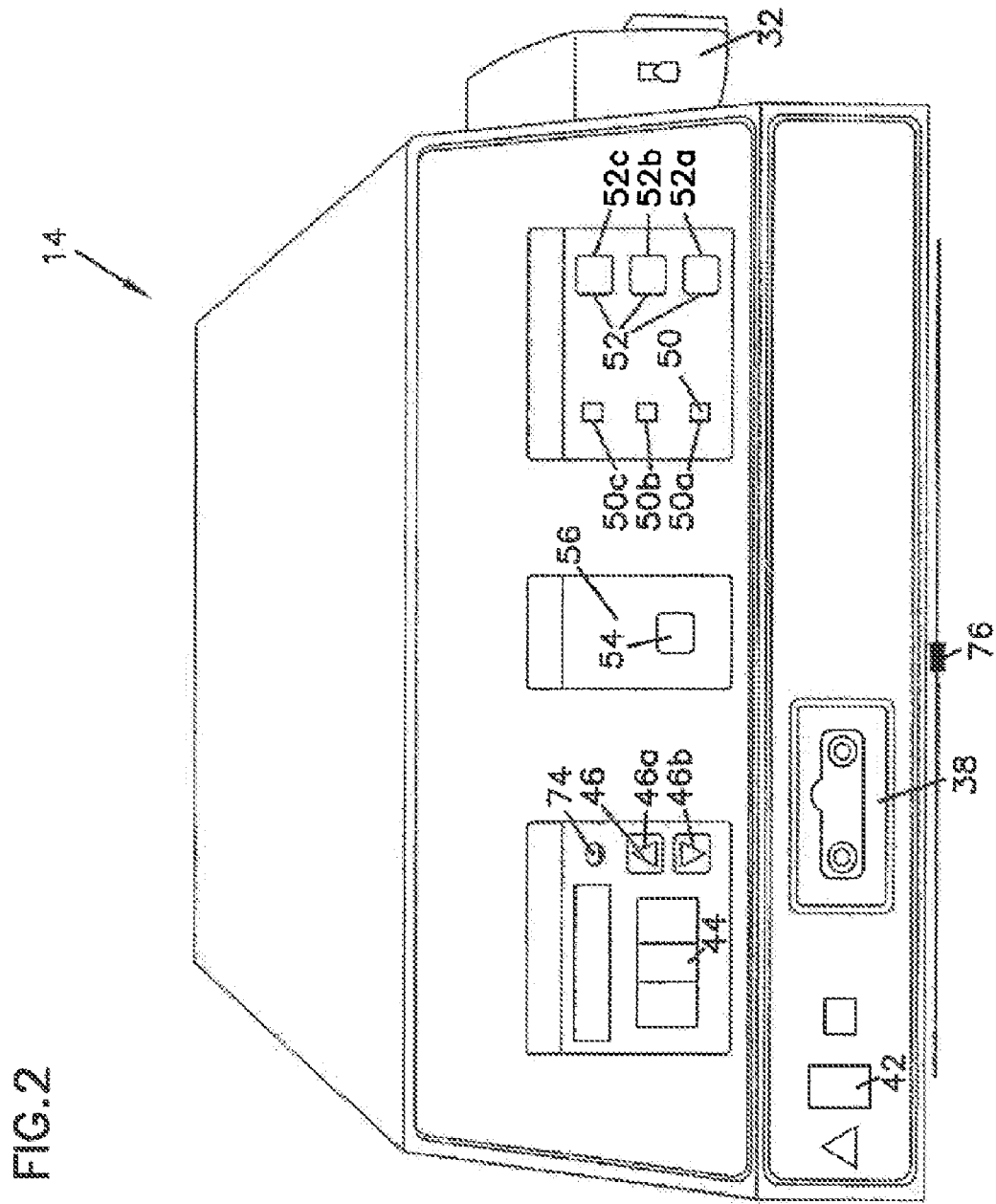
FIG. 2 is a front perspective view of the electrosurgical unit of FIG. 1.

As shown in FIG. 1, electrosurgical device 30 is connected to electrosurgical unit 14 via a cable 34 which comprises a plurality of electrically insulated wire conductors and at least one plug 36 at the end thereof. The electrosurgical unit 14 provides radio-frequency (RF) energy/power via cable 34 to electrosurgical device 30. As shown in FIG. 2, plug receptacle 38 of electrosurgical unit 14 receives the plug 36 of device 30 therein to electrically connect device 30 to the electrosurgical unit 14. Preferably the fluid delivery tubing 28 is provided as part of cable 34 and produced with the electrically insulated wires via plastic co-extrusion.

FIG. 2 shows the front panel of the electrosurgical unit 14. A power switch 42 is used to turn the electrosurgical unit 14 on and off. After turning the electrosurgical unit 14 on, the RF power setting display 44 is used to display the RF power setting numerically in watts. Preferably the power setting display comprises a liquid crystal display (LCD). Additionally, this display 44 is used to display errors, in which case the display 44 will show "Err" and blink alternately with a special error code number(s).

The RF power selector comprises RF power setting switches 46a, 46b which are used to select the RF power setting. Pushing the switch 46a increases the RE power setting, while pushing the switch 46b decreases the RF power setting. RF power output may be set in 5 watt increments in the range of 20 to 100 watts, and 10 watt increments in the range of 100 to 200 watts. Additionally, electrosurgical unit 14 includes an RE power activation display 74 comprising an indicator light which illuminates when RF power is activated. Switches 46a, 46b may comprise membrane switches.

In addition to having a RF power setting display, electrosurgical unit 14 further includes a fluid flow rate setting display. Flow rate setting display comprises three indicator lights 50a, 50b and 50c with a first light 50a corresponding to a fluid flow rate setting of low, a second light 50b corresponding to a fluid flow rate setting of medium (intermediate) and a third light 50c corresponding to a flow rate setting of high. One of these three indicator lights will illuminate when a fluid flow rate setting is selected.

A fluid flow selector comprising flow rate setting switches 52a, 52b and 52c are used to select or switch the flow rate setting. Three push switches are provided with the first switch 52a corresponding to a fluid flow rate setting of low, the second switch 52b corresponding to a fluid flow rate setting of medium (intermediate) and the third switch 52c corresponding to a flow rate setting of high. Pushing one of these three switches selects the corresponding flow rate setting of either low, medium (intermediate) or high. The medium, or intermediate, flow rate setting is automatically selected as the default setting if no setting is manually selected. Switches 52a, 52b and 52c may comprise membrane switches.

Before starting a surgical procedure, it is desirable to prime device 30 with fluid 24. Priming is desirable to inhibit RF power activation without the presence of fluid 24. A priming switch 54 is used to initiate priming of device 30 with fluid 24. Pushing switch 54 once initiates operation of pump 32 for a predetermined time period to prime device 30. After the time period is complete, the pump 32 shuts off automatically. When priming of device 30 is initiated, a priming display 56 comprising an indicator light illuminates during the priming cycle.

On the front panel the bipolar activation display 74 illuminates when RF power is activated from the electrosurgical unit 14, either via a hand switch 162 on device 30 (as shown in FIG. 1) or a footswitch (not shown). A pullout drawer 76 is located under the electrosurgical unit 14 where the user of electrosurgical unit 14 may find a short form of the user's manual.

Figure 3:
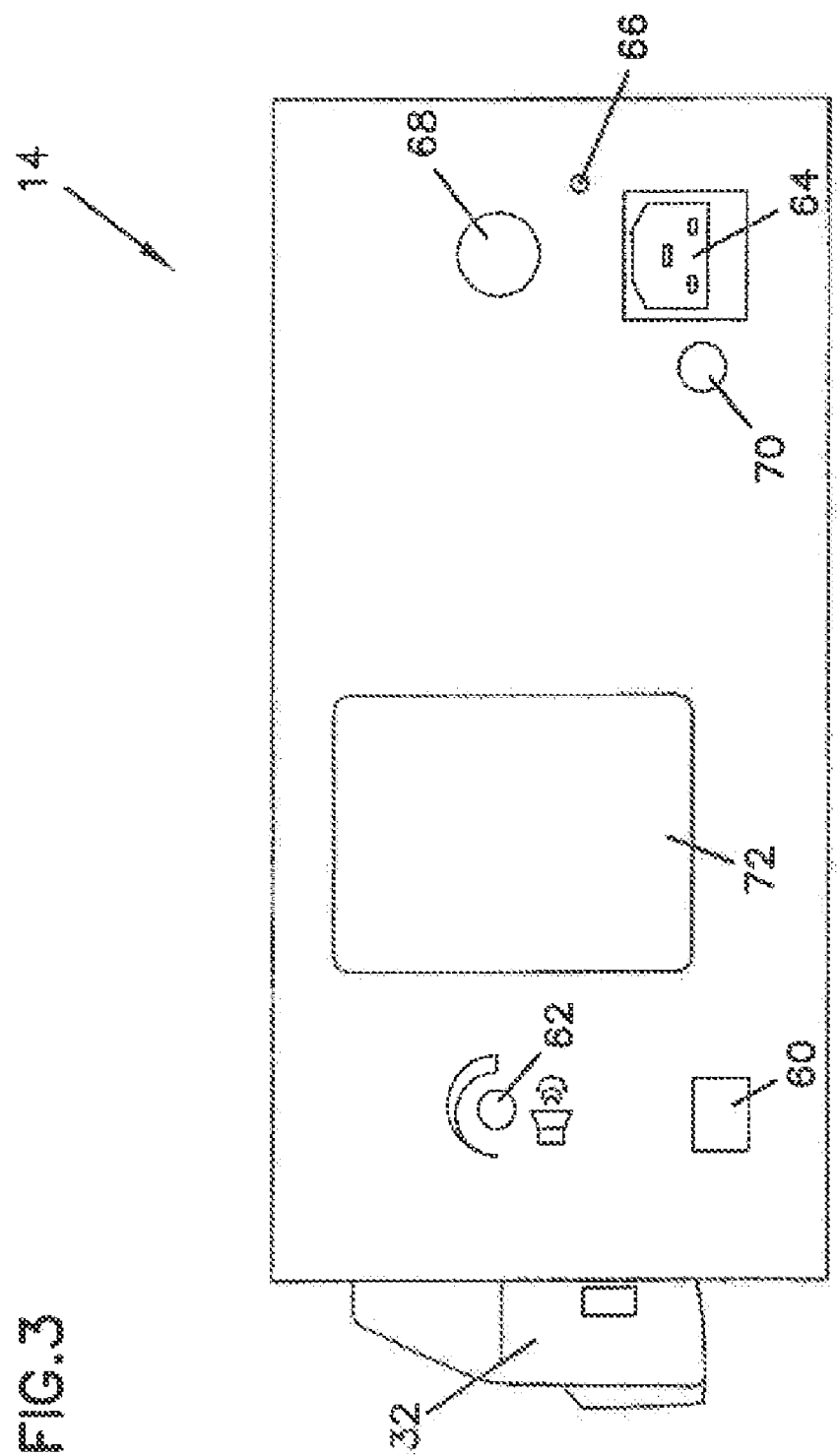
FIG. 3 is a rear view of the electrosurgical unit of FIG. 1.

FIG. 3 shows the rear panel of electrosurgical unit 14. The rear panel of the electrosurgical unit 14 includes a speaker 60 and a volume control knob 62 to adjust the volume of the tone that will sound when the RF power is activated (RF power activation tone). The volume of the RF power activation tone is increased by turning the knob clockwise, and decreased by turning the knob counterclockwise. However, the electrosurgical unit 14 prevents this tone from being completely silenced.

Rear panel of electrosurgical unit 14 also includes a power cord receptacle 64 used to connect the main power cord to the electrosurgical unit 14 and an equipotential grounding lug connector 66 used to connect the electrosurgical unit 14 to earth ground using a suitable cable. The rear panel also includes a removable cap 68 for the installation of a bipolar footswitch socket connectable to an internal footswitch circuit of electrosurgical unit 14 so that the RF power may be activated by a footswitch in addition to a handswitch of device 30. Additionally, the rear panel also includes a fuse drawer 70 which includes which contains two extra fuses, consistent with the line voltage. Finally, the rear panel includes a name plate 72 which may provide information such as the model number, serial number, nominal line voltages, frequency, current and fuse rating information of the electrosurgical unit 14.

Figure 4:
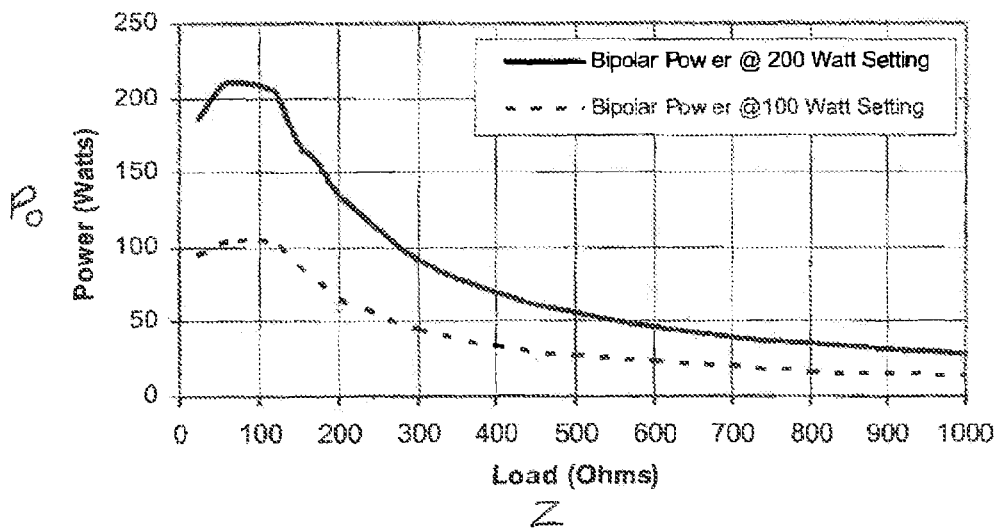
FIG. 4 is a graph of the RF power output $P_o$ versus impedance Z for the electrosurgical unit of FIG. 1.

The RF power output curve of electrosurgical unit 14 is shown in FIG. 4. Impedance Z, shown in units of ohms on the X-axis and output power $P_O$ is shown in units of watts on the Y-axis. In the illustrated embodiment, the bipolar electrosurgical power (RF) is set to 200 watts. As shown in the figure, for an RF power setting $P_S$ of 200 watts, the output power $P_O$ will remain constant with the set RF power $P_S$ as long as the impedance Z stays between the low impedance cut-off of 30 ohms and the high impedance cut-off of 125 ohms. Below an impedance Z of 30 ohms, the output power $P_O$ will decrease as shown by the low impedance ramp. Above an impedance Z of 250 ohms, the output power $P_O$ will also decrease as shown by the high impedance ramp.

Figure 5:
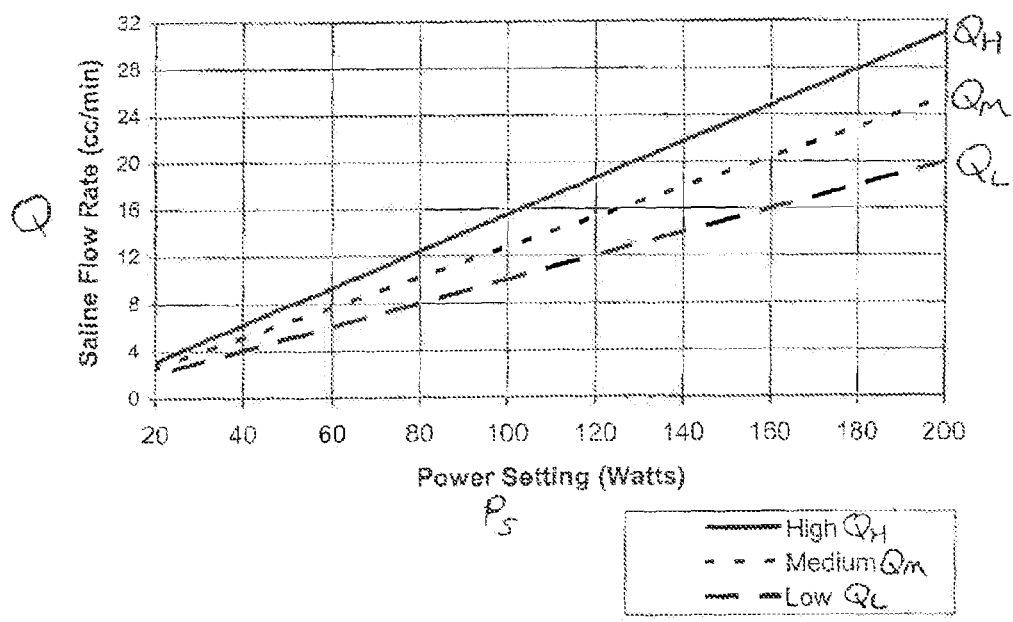
FIG. 5 is graph showing three relationships of fluid flow rate Q of saline (at high $Q_H$, medium $Q_M$ and low $Q_L$) in units of cubic centimeters per minute (cc/min) on the Y-axis, and the RF power setting $P_S$ in units of watts on the X-axis.

Electrosurgical unit 14 has also been configured such that the pump speed, and therefore the throughput of fluid expelled by the pump, is predetermined based on two input variables, the RF power setting and the fluid flow rate setting. In FIG. 5 there is shown a relationship of fluid flow rate Q in units of cubic centimeters per minute (cc/min) on the Y-axis, and the RF power setting $P_S$ in units of watts on the X-axis. The relationship has been engineered to inhibit undesirable effects such as tissue desiccation, electrode sticking, smoke production and char formation, while at the same time providing a fluid flow rate Q at a corresponding RF power setting $P_S$ which is not so great as to provide too much fluid and associated electrical dispersion and cooling at the electrode-tissue interface. While not being bound to a particular theory, a more detailed discussion on how the fluid flow rate interacts with the radio frequency power, modes of heat transfer from the tissue, fractional boiling of the fluid and various control strategies may be found in U.S. Publication No. 2001/0032002, published Oct. 18, 2001, and assigned to the assignee of the present invention and hereby incorporated by reference in its entirety to the extent it is consistent.

As shown, electrosurgical unit 14 has been configured to increase the fluid flow rate Q linearly with an increasing RF power setting $P_S$ for each of three fluid flow rate settings of low, medium and high corresponding to $Q_L$, $Q_M$ and $Q_H$, respectively. Conversely, electrosurgical unit 14 has been configured to decrease the fluid flow rate Q linearly with a decrease RF power setting $P_S$ for each of three fluid flow rate settings of low, medium and high corresponding to $Q_L$, $Q_M$ and $Q_H$, respectively. As shown, $Q_L$, $Q_M$ and $Q_H$ can be expressed as a function of the RF power setting $P_S$ by changing exemplary proportionality constants as follows:

$$Q_L = 0.1 \times P_S$$

$$Q_M = 0.1286 \times P_S$$

$$Q_H = 0.1571 \times P_S$$

FIG. 6 shows an exemplary block diagram of how electrosurgical unit 14 processes the inputs of RF power setting $P_S$ and the fluid flow rate setting, either $Q_L$, $Q_M$ or $Q_H$, to control the pump speed, and therefore the throughput of fluid expelled by the pump 32. As shown, user selected input values for the RF power setting $P_S$ and the fluid flow rate setting of either low, medium and high (corresponding to $Q_L$; $Q_M$ and $Q_H$), as well as activating the priming function, are entered into electrosurgical unit 14 by pushing corresponding switches for these parameters positioned on the front panel of the electrosurgical unit 14.

As shown in FIG. 6, the RF power setting switches 46a, 46b, the flow rate setting switches 52a, 52b, 52c and the priming switch 54 are a display panel module 40, preferably comprising a printed circuit board, which receives the inputs into electrosurgical unit 14.

The user selected input values for RF power, fluid flow rate and priming are then conveyed via corresponding input signals 41 to a main module 43 which preferably comprises a printed circuit board including a computer chip 45, a radio-frequency generator 47 and a pump controller 48. As shown, display panel module 40 and main module 43, as well as other components receive power from a power supply module 49, which also comprises a printed circuit board.

Computer chip 45 preferably comprises a micro-processor unit, a memory, and an input/output control unit. In this manner, the functional relationships between the radio-frequency power level and the flow of the fluid may be stored in the memory of the computer chip 45. While the functional relationships may be stored in the form of the foregoing equations, they may also be stored as numerical data points as part of a database look-up table.

As shown, the input signals 41 are received and processed by computer chip 45. More specifically, for example, from the input signal received corresponding to the fluid flow rate setting of either $Q_L$, $Q_M$ or $Q_H$, the computer chip 45 may first determine which of the above equations to apply. After determining which equation to apply, computer chip 45 may then apply the relationship to determine the output for flow of the fluid from the pump 32 based on the selected radio-frequency power level. Having determined this output, the computer chip 45 then sends output signals 51 and 53 corresponding to the selected radio-frequency power level and calculated output for flow of the fluid from the pump 32 to the radio-frequency generator 47 and pump controller 48, respectively. Thereafter, the pump controller 48 controls the speed of the pump drive shaft 55 by controlling the input voltage 59 to the pump motor 61 which rotates the drive shaft 55. More detailed drawings of exemplary electrosurgical unit 14 may be found in U.S. Publication No. 2006/0149225, published Jul. 6, 2006, and assigned to the assignee of the present invention and hereby incorporated by reference in its entirety to the extent it is consistent.

Electrosurgical unit 14 can include a delay mechanism, such as a timer, to automatically keep the fluid flow on for several seconds after the RF power is deactivated to provide a post-treatment cooling. Electrosurgical unit 14 can also include a delay mechanism, such as a timer, to automatically turn on the fluid flow up to several seconds before the RF power is activated to inhibit the possibility of undesirable effects as tissue desiccation, electrode sticking, char formation and smoke production.

Electrosurgical unit 14 is particularly configured for use with bipolar devices. With a bipolar device, an alternating current is created between the first and second electrical poles of the device. An exemplary bipolar electrosurgical device of the present invention which may be used in conjunction with electrosurgical unit 14 of the present invention is shown at reference character 30a in FIG. 7. While various electrosurgical devices of the present invention are described herein with reference to use with electrosurgical unit 14, it should be understood that the description of the combination is for purposes of illustrating the system of the invention. Consequently, it should be understood that while the electrosurgical devices disclosed herein may be preferred for use with electrosurgical unit 14, it may be plausible to use other electrosurgical devices with electrosurgical unit 14 such as monopolar devices, or it may be plausible to use the electrosurgical devices disclosed herein with another electrosurgical unit other than electrosurgical unit 14.

Figure 7:
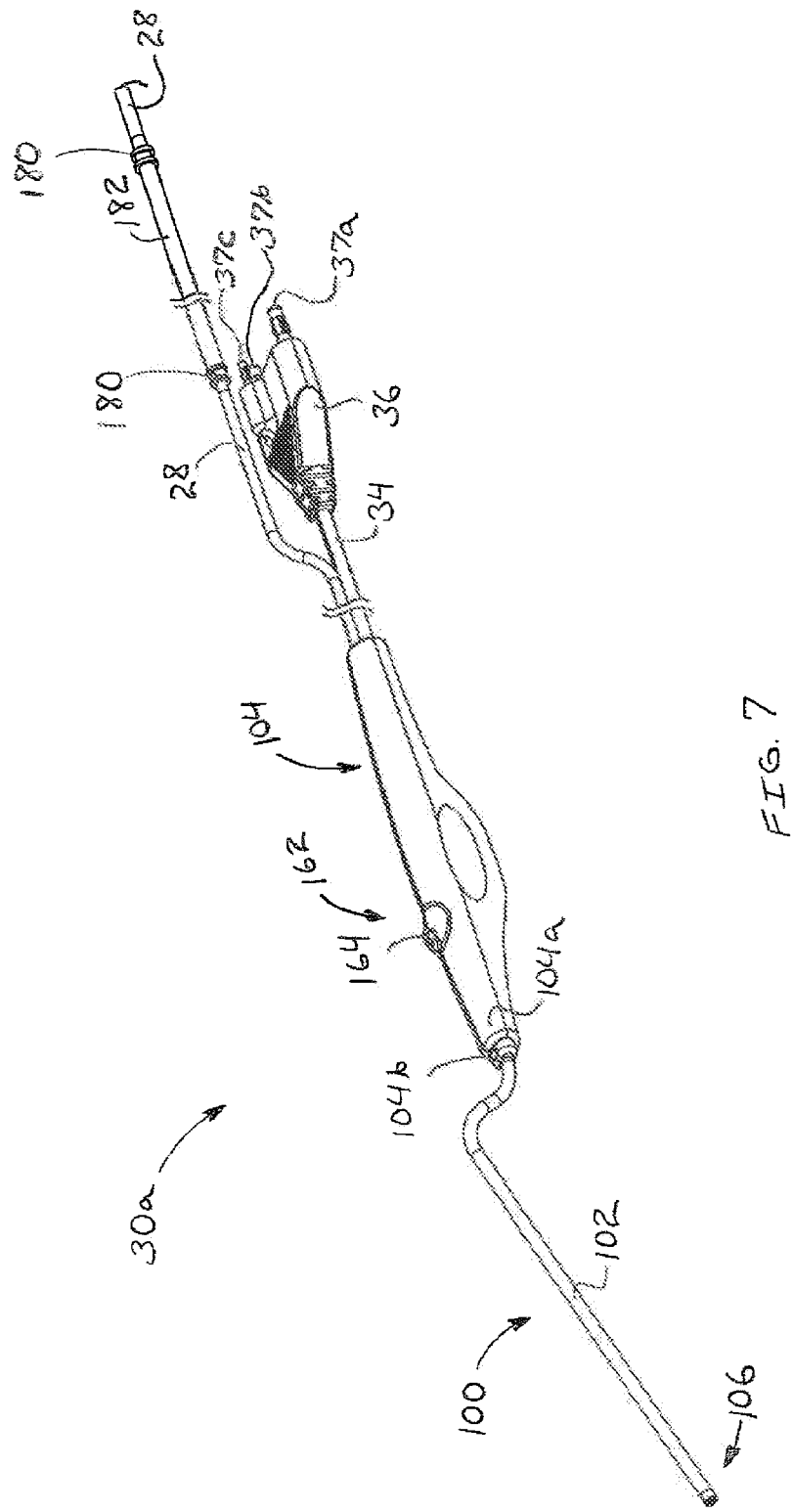
FIG. 7 is an isometric view of an assembly of an exemplary electrosurgical device according to the present invention.

As shown in FIG. 7, exemplary bipolar electrosurgical device 30a comprises a single stationary arm 100 which comprises a rigid, self-supporting, hollow shaft 102. As shown, shaft 102 is preferably angled to provide better viewing of the distal tip portion 106 of device 30a during use thereof. Shaft 102 preferably comprises metal tubing, and more preferably thick walled hypodermic stainless steel tubing. In this manner, shaft 102 has sufficient rigidity to maintain its form during use of device 30a without kinking or significant bending, and support the distal portion 106 in rigid relation to a proximal handle 104. In other embodiments, shaft 102 may be made of an electrical non-conducting material, such as a polymer or composite material.

Proximal handle 104 comprises mating handle portions 104a, 104b. Handle 104 is preferably made of a sterilizable, rigid, non-conductive material, such as a polymer. Also, handle 104 is preferably configured slender, along with the rest of the device 30a, to facilitate a user of device 30a to hold and manipulate device 30a like a pen-type device.

Device 30a also comprises a flexible fluid delivery tubing 28 which is connectable to fluid source 22, preferably via a spike located at the end of drip chamber 26 (as shown in FIG. 1), and a cable 34 which is connectable to electrosurgical unit 14, which respectively provide fluid and RF power to distal portion 106.

Figure 8:
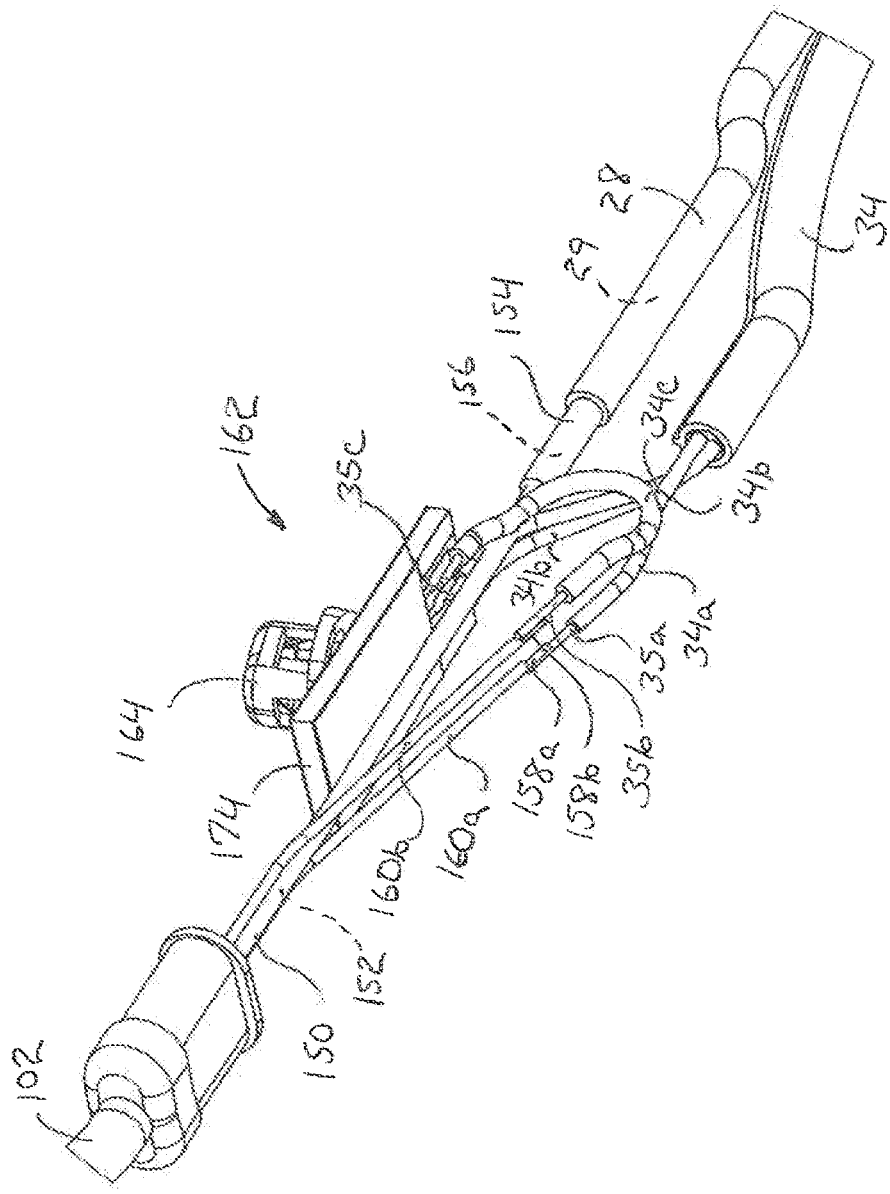
FIG. 8 is an isometric view of the inner components of the handle with the handle removed.

In this embodiment, cable 34 of device 30a comprises three insulated wires 34a, 34b, 34c (as shown in FIG. 8) connectable to electrosurgical unit 14 via three (male) plug connectors 37a, 37b, 37c. The plug connectors 37a, 37b, 37c are each assembled with wires 34a, 34b, 34c and wire conductors 35a, 35b, 35c within a common plug housing 36. As best shown in FIG. 8, which shows the inner components of the handle 104 with the handle 104 removed, wire conductor 35a is directly connected, preferably by welding, to wire conductor 158a of insulated wire 160a, which is distally connected to electrode 114a as discussed in greater detail below. As also shown in FIG. 8, wire conductor 35b of wire 34b first connects through hand switch assembly 162 before connecting, preferably be welding, to wire conductor 158b of insulated wire 160b, which is distally connected to electrode 114b as discussed in greater detail below. Finally, wire conductor 35c of wire 34c is connected to hand switch assembly 162 to alert electrosurgical unit 14 to provide power when the circuit for the switch assembly has been closed through depression of hand switch push button 164, preferably made of a rigid polymer such as polyacetal.

Figure 9:
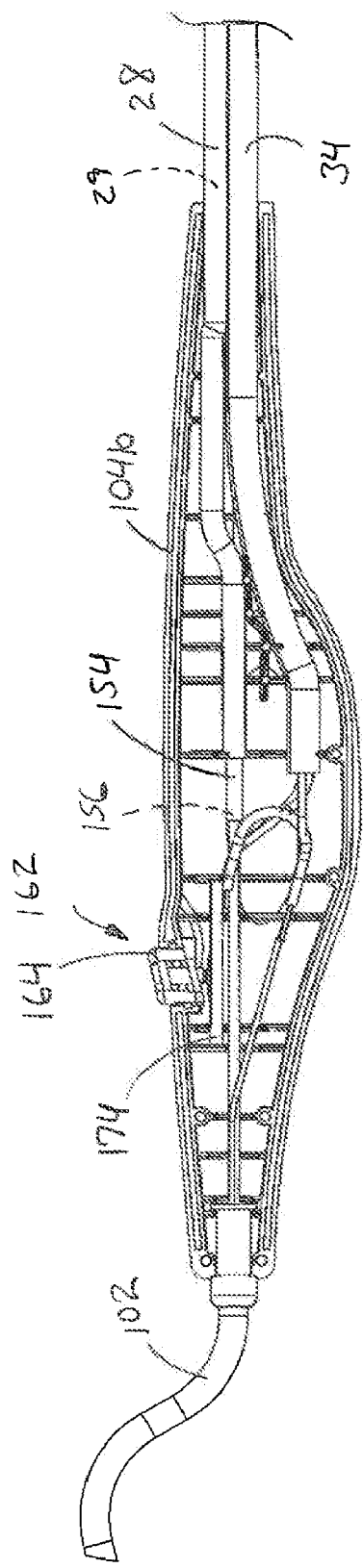
FIG. 9 is a side view of a handle portion of the device of FIG. 7 assembled with various components.
Figure 10:
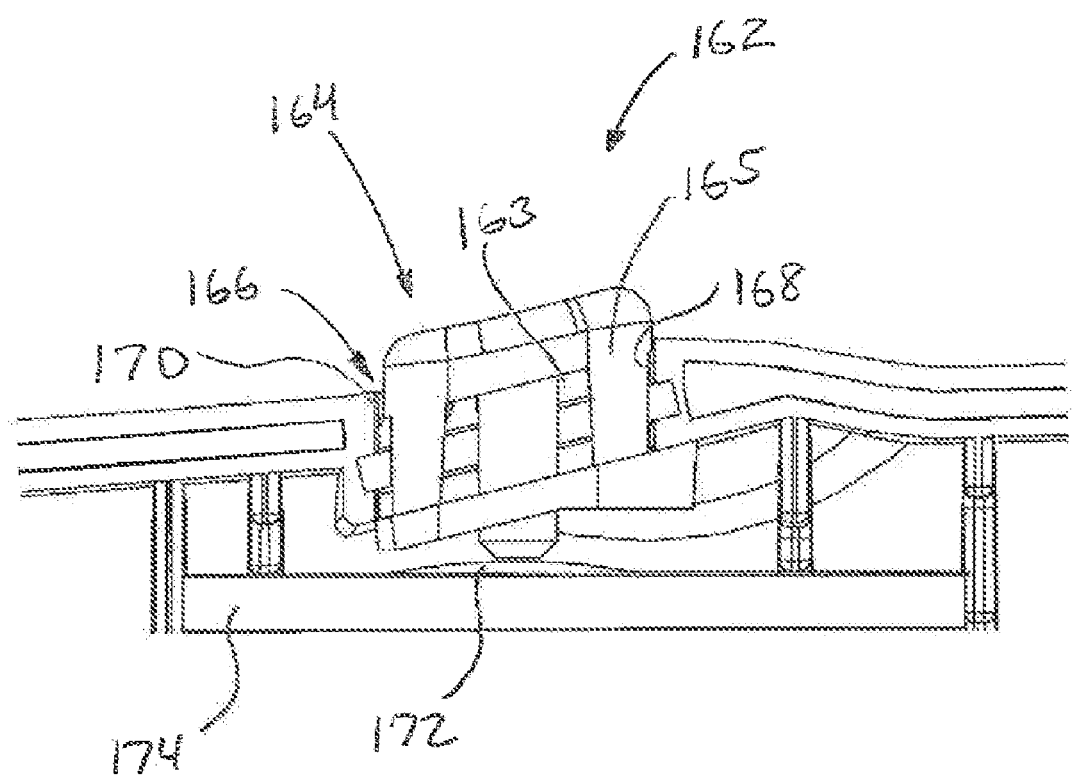
FIG. 10 is a close-up side view of a button and handle portion of the device of FIG. 7 assembled with various components.

In addition to FIG. 8, switch assembly 162 is shown in FIGS. 9 and 10. As best shown in FIG. 10, switch assembly 162 comprises a push button 164 and a dome switch 172 having two electrical contacts. The contacts preferably comprise upper and lower contacts disposed on a platform 174 in overlying relationship. Preferably the upper contact comprises a dome shaped configuration overlying and spaced from the lower contact which is flat. Preferably the contacts are spaced from one another by virtue of the domed configuration of the upper contact when the button 164 is in an undepressed position, thus creating an open control circuit relative to switch 172. However, when the top of button 164 is pressed, and the upper contact is correspondingly pressed into a depressed position, the upper contact comes into contact with the lower contact thus closing the hand switch control circuit. The presence of the closed control circuit is then sensed by electrosurgical unit 14 which then provides power to the electrodes 114a, 114b.

When a depression force is removed from the upper contact, the contact returns to its undepressed domed position as a result of its resiliency or elastic memory, thus returning button 164 to its undepressed position and reopening the hand control circuit. The presence of the open control circuit is then sensed by electrosurgical unit 14 which then stops providing power to electrodes 114a, 114b. More detailed drawings and an explanation of the operation of switch assembly 162 may be found in U.S. Publication No. 2005/0090816, published Apr. 28, 2005, and assigned to the assignee of the present invention and hereby incorporated by reference in its entirety to the extent it is consistent.

During use of device 30a, blood and coagulum may deposit in a narrow gap 170 between button 164 and handle 104. As best shown in FIG. 10, button 164 is located in aperture 166 of handle 104 which is defined by a perimeter wall 168. As shown, button 164 includes a plurality of apertures 163 in the sides thereof. Apertures 163 reduce the surface area of the side walls 165 of button 164 adjacent to the perimeter wall 168 of handle portions 104a, 104b. Consequently, due to the reduced surface area of the side walls 165 of button 164, button 164 is less apt to adhere and stick to handle portions 104a, 104b, by virtue of the blood and coagulum, when the depression force is removed from button 164.

Figure 11:
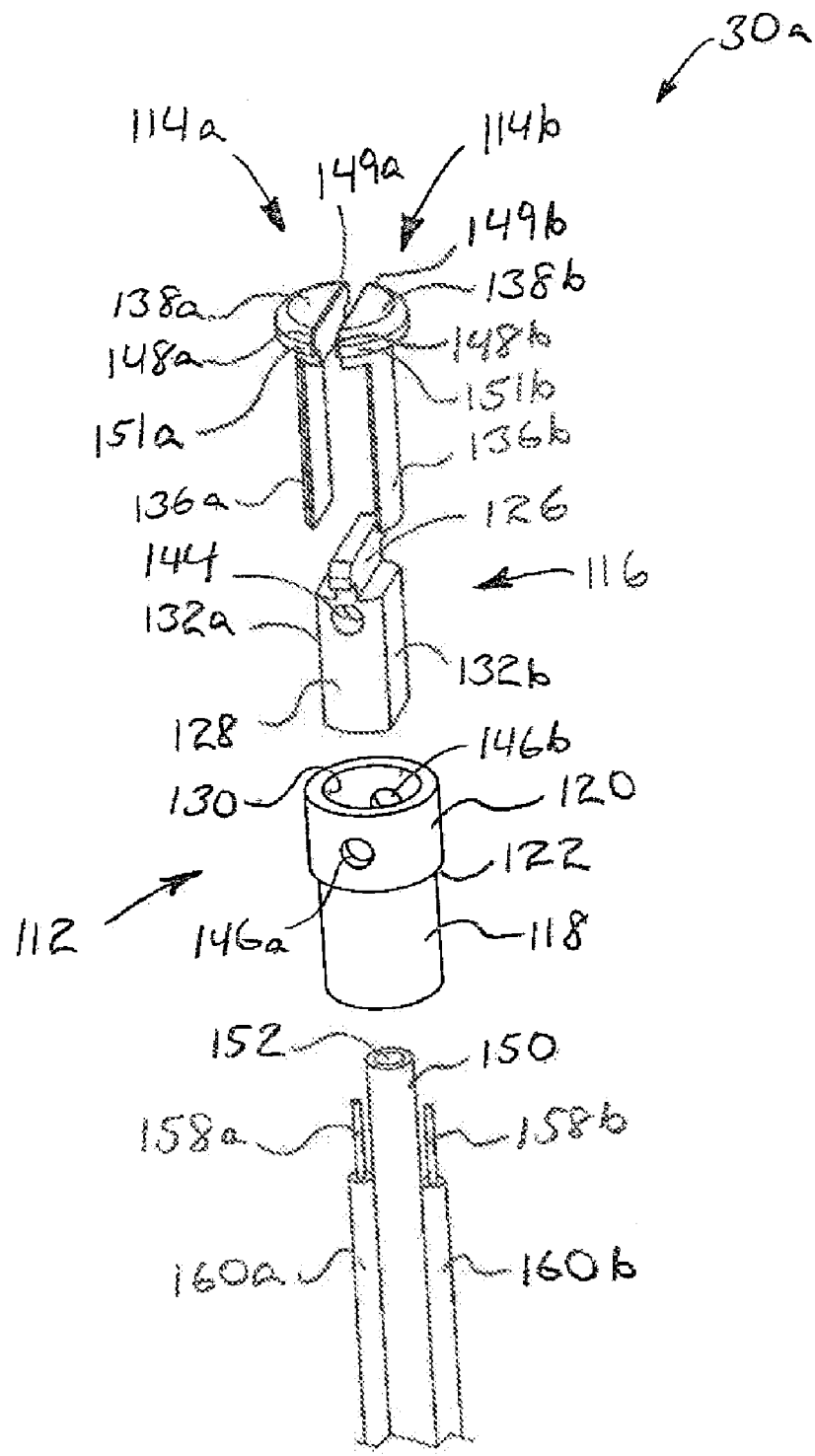
FIG. 11 is an exploded view of a distal portion of the device of FIG. 7.

As best shown in FIG. 11, device 30a has a disc shaped distal end comprising two bipolar electrodes 114a, 114b. An insulator housing assembly comprising housing outer portion 112 and housing inner portion 116 secures the electrodes 114a, 114b to device 30a. Housing outer portion 112 and housing inner portion 116 comprise an electrically insulative material, preferably a polymer and more preferably a fluorinated polymer such as polytetrafluoroethylene (PTFE). In addition to functioning as an electrical insulator, polytetrafluoroethylene is preferred because it is hydrophobic and thus inhibits fluids present during surgery from settling thereon, provides good arc resistance, and provides a low coefficient of friction for reduced tissue sticking.

Figure 12:
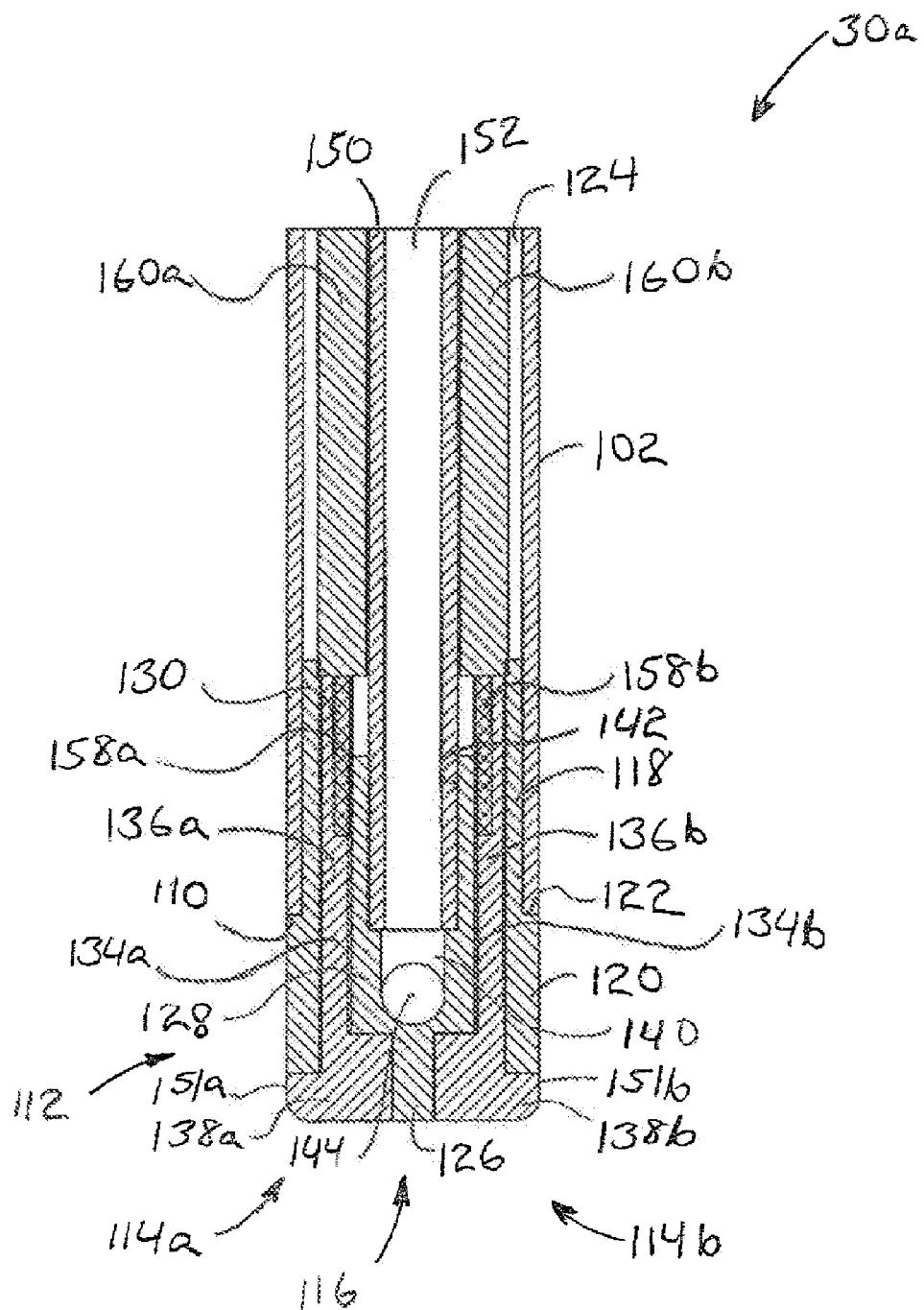
FIG. 12 is a close-up longitudinal cross-sectional view of a distal portion of the device of FIG. 7.

As shown in FIG. 12, housing outer portion 112 electrically insulates electrodes 114a, 114b from metal shaft 102. As shown in FIGS. 11 and 12, housing outer portion 112 comprises a proximal cylindrical portion 118 and a distal cylindrical portion 120. Proximal cylindrical portion 118 has a slightly small outer diameter than distal cylindrical portion 120, which creates a rim 122 there between. For assembly, proximal cylindrical portion 118 provides a connector portion for connecting housing outer portion 112 to shaft 102. As shown in FIG. 12, the outside diameter of proximal cylindrical portion 118 is configured to extend into lumen 124 of shaft 102 and fit with the inside diameter of shaft 102, with rim 122 in contact with the distal end 110 of shaft 102. The outside diameter of proximal cylindrical portion 118 may be configured to fit with the inside diameter of shaft 102 to form a slip fit, in which case adhesive or another bonding agent will be employed between cylindrical portion 118 and shaft 102 to provide a secure connection, or a press (interference) fit which would not require the use of a separate bonding agent.

As shown in FIGS. 11 and 12, housing inner portion 116 electrically insulates electrodes 114a, 114b from one another by providing a spacer there between. In particular, housing inner portion 116 comprises a distal spacer portion 126 disposed between electrodes 114a and 114b. For assembly, housing inner portion 116 further comprises a proximal cylindrical portion 128 for connecting housing inner portion 116 to housing outer portion 112. As shown in FIG. 12, the outside diameter of proximal cylindrical portion 128 is configured to extend into inner bore 130 of housing outer portion 112 and fit with the diameter of bore 130, with the distal cylindrical portion 120 of housing outer portion 112 providing a collar around housing inner portion 116 and electrodes 114a, 114b. The outside diameter of proximal cylindrical portion 128 may be configured to fit with the diameter of bore 130 to form a slip fit, in which case adhesive or another bonding agent will be employed between cylindrical portion 128 and housing outer portion 112 to provide a secure connection, or a press (interference) fit which would not require the use of a separate bonding agent.

In addition to the above, as best shown in FIG. 11, proximal cylindrical portion 128 of housing inner portion 116 is provided with two opposing flat surfaces 132a, 132b formed thereon to create two localized gaps 134a, 134b, as shown in FIG. 12, between housing outer portion 112 and housing inner portion 116 through which legs 136a, 136b of electrodes 114a, 114b may extend to be connected with wire conductors 158a, 158b of insulated wires 160a, 160b.

Returning to FIG. 11, legs 136a, 136b of electrodes 114a, 114b extend proximally from two semi-circular shaped electrode portions 138a, 138b located at the distal end of device 30a and having the same size and shape. In this manner, the current density exhibited by the electrodes relative to one another will be substantially uniform. Also as shown, the semi-circular electrode portions are mirror images of each other and each comprises the shape of about half of a circle. Electrodes 114a, 114b preferably comprise an electrically conductive metal, which is also preferably non-corrosive. A preferred material is stainless steel. Other suitable metals include titanium, gold, silver and platinum.

Figure 13:
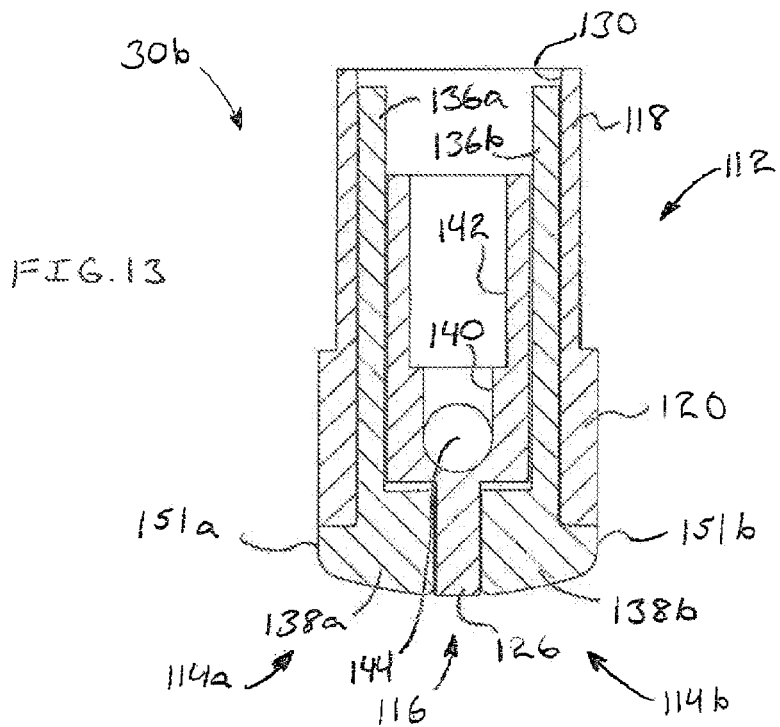
FIG. 13 is a close-up longitudinal cross-sectional view of a distal portion of an alternative exemplary electrosurgical device according to the present invention.
Figure 14:
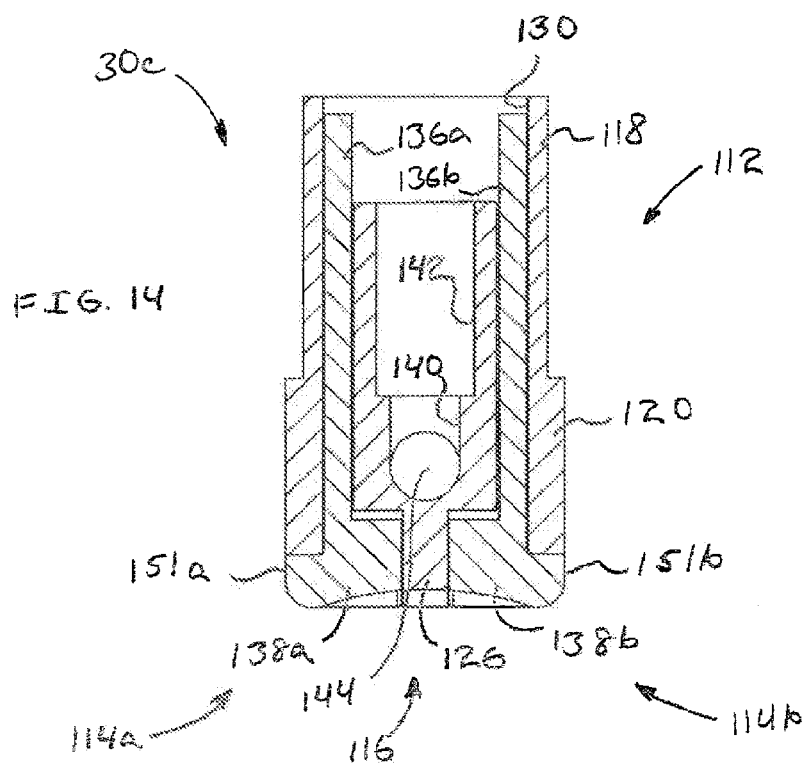
FIG. 14 is a close-up longitudinal cross-sectional view of a distal portion of an alternative exemplary electrosurgical device according to the present invention.

As shown in FIG. 12, the distal end of device 30a is planar (flat), and perpendicular to the longitudinal axis of shaft 102. In other embodiments, as shown, for example, in FIG. 13, the distal end of device 30b may be convex. In still other embodiments, as shown, for example, in FIG. 14, the distal end of device 30c may be concave.

Returning to FIG. 12, housing inner portion 116 also includes a longitudinally oriented linear blind bore 140 and counter bore 142 centrally located within cylindrical portion 128. As shown, the outside diameter of fluid delivery tubing 150 is configured to extend into counter bore 142 and fit with the diameter of counter bore 142, with the distal end of the tubing in contact with the bottom of the counter bore. The outside diameter of fluid delivery tubing 150 may be configured to fit with the diameter of counter bore 142 to form a press (interference) fit to provide a secure connection along with use of an adhesive or another bonding agent to provide a fluid tight seal between fluid delivery tubing 150 and housing inner portion 116.

In addition to blind bore 140 and counterbore 142, housing inner portion 116 also includes a linear through bore 144 which perpendicularly intersects bore 140 at the distal end of bore 140 and extends through cylindrical portion 128. As shown, bore 140 and bore 144 are in fluid communication with lumen 152 of fluid delivery tubing 150 which is ultimately in fluid communication lumen 29 of fluid delivery tubing 28. In this manner, bore 140 and bore 144 provide a T shaped fluid flow passage for fluid 24 provided from fluid delivery tubing 28 and 150.

As shown in FIG. 11, in order to have fluid from the fluid passage provided by bore 144 exit device 30a, cylindrical portion 120 of housing outer portion 112 is provided with two through holes 146a, 146b which align with bore 144 and provide fluid exits for fluid. As shown bore 144 extends through housing inner portion 116 parallel to distal spacer portion 126.

As best shown in FIG. 11, holes 146a, 146b are provided in the electrically insulative material used for housing outer portion 112 and are located on the distal portion of device 30a proximal to the distal end of the device. In this manner, holes 146a, 146b are configured to inhibit clogging during use of the device 30a. In other words, since housing outer portion 112 is not electrically conductive, and does not function as an electrode, tissue and blood coagulum are less apt to stick to housing outer portion 112. Also, since holes 146a, 146b are located on the distal portion of device 30a proximal to the distal end of the device, holes 146a, 146b are less apt to be exposed directly to the bloody field generally located at the distal end of device 30a.

In the event holes 146a, 146b and bore 144 become clogged, holes 146a, 146b and bore 144 may be unclogged and cleaned by inserting a pin type structure into one of the holes and bore 144, and extending the pin completely through device 30a and exiting the pin from the other hole. In this manner, the matter clogging holes 146a, 146b and bore 144 may be pushed and removed there from by the pin.

Also as shown in FIG. 11, holes 146a, 146b are located on opposing sides of device 30a. Hole 146a is provided adjacent and closest to electrode 114a at corner 148a thereof, and adjacent and closest to electrode 114b at corner 148b thereof. Hole 146b is provided adjacent and closest to electrode 114a at corner 149a thereof and adjacent and closest to electrode 114b at corner 149b thereof. In this manner, fluid may be provided to the locations of electrodes 114a, 114b and tissue expected to have the greatest need for the fluid for device 30a to function most properly (i.e. the electrode corners and tissue adjacent thereto). Also in this manner, fluid from holes 146a, 146b may be provided to the semi-circular shaped side perimeter 151a, 151b of electrodes 114a, 114b. As shown in FIG. 12, the semi-circular shaped perimeter 151a, 151b of electrodes 114a, 114b is exposed to tissue and extends circumferentially around a substantial portion of the distal end of device 30a. As shown, the semi-circular shaped perimeter 151a of electrode 114a extends from corner 148a to corner 149a of electrode 114a, and the semi-circular shaped perimeter 151b of electrode 114b extends from corner 148b to corner 149b of electrode 114b.

Figure 15:
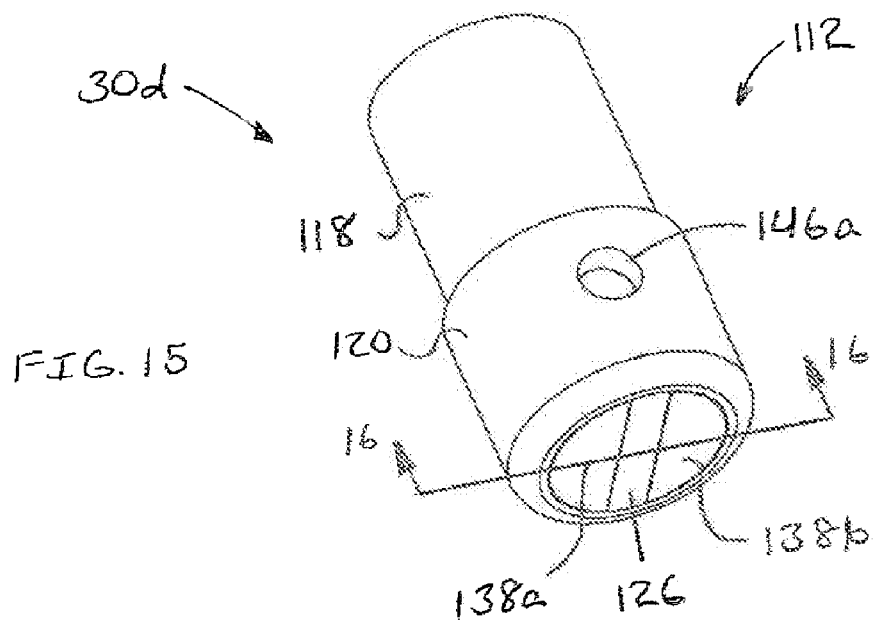
FIG. 15 is an isometric view of a distal portion of an alternative exemplary electrosurgical device according to the present invention.
Figure 16:
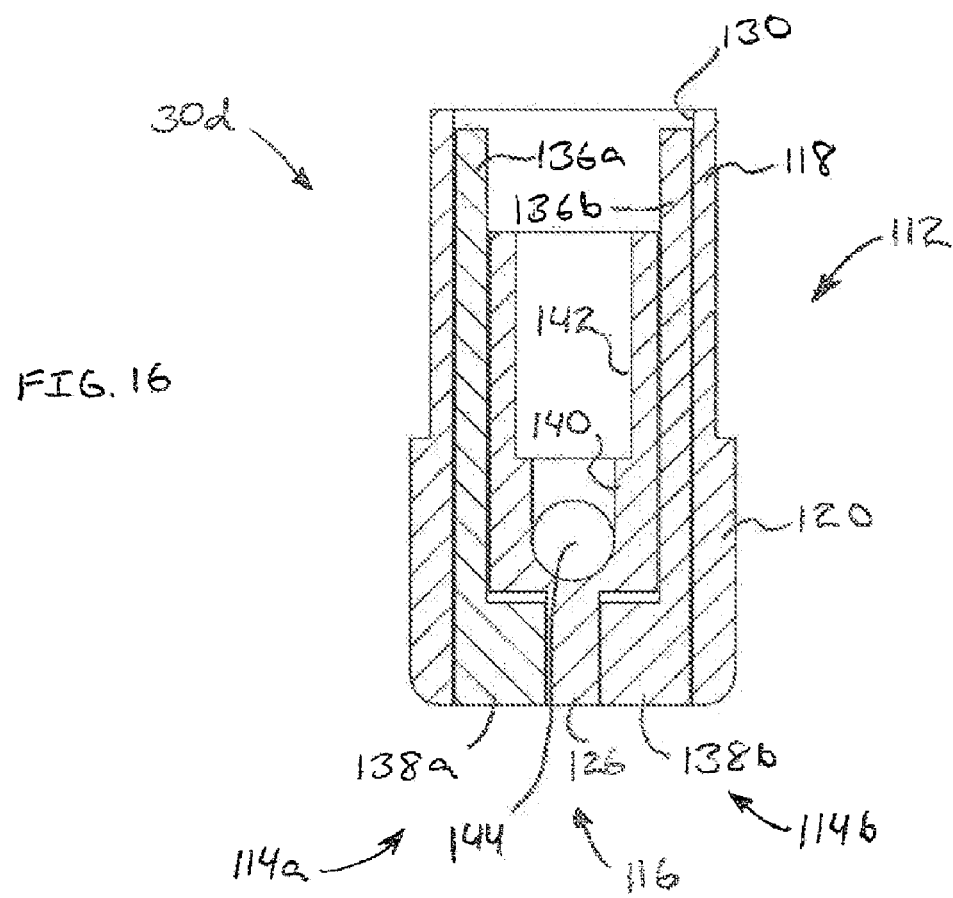
FIG. 16 is a close-up longitudinal cross-sectional view of the distal portion of the device of FIG. 15 taken along line 16-16.

In other embodiments, as shown in FIGS. 15 and 16, the semi-circular shaped side perimeter 151a, 151b of electrodes 114a, 114b for device 30d is covered by an electrical insulation, preferably provided by outer housing portion 112, to eliminate the semi-circular shaped perimeter 151a, 151b of electrodes 114a, 114b from being used to treat tissue. As shown, the semi-circular shaped perimeter 151a, 151b of electrodes 114a, 114b is covered by a ring shaped portion of outer housing portion 112.

During use of device 30a, fluid 24 from fluid source 22 is communicated through a fluid passage which provided by various structures. Fluid 24 from the fluid source 22 is first communicated through lumen 29 of delivery tubing 28. As shown in FIG. 8, fluid 24 then feeds into a lumen 156 of a size reduction bushing 154 located within handle 104, and then into lumen 152 of tubing 150, which is contained in the lumen 124 of shaft 102 as shown in FIG. 12. From lumen 152 of tubing 150, fluid 24 then flows through bore 140, then into bore 144 and is expelled from holes 146a, 146b. In the present embodiment, which makes use of a peristaltic pump 32, a special pump tubing segment 182, as shown in FIG. 7, designed to operate specifically with the peristaltic pump 32 may be spliced in between portions of delivery tubing 28 and connected thereto using barbed fluid line connectors 180 at each end thereof.

The relationship between the material for electrodes 114a, 114b and their surfaces, and fluid 24 throughout the various embodiments should be such that the fluid 24 wets the surface of the electrodes 114a, 114b. Contact angle, θ, is a quantitative measure of the wetting of a solid by a liquid. It is defined geometrically as the angle formed by a liquid at the three phase boundary where a liquid, gas and solid intersect. In terms of the thermodynamics of the materials involved, contact angle θ involves the interfacial free energies between the three phases given by the equation $$\gamma_{LV} \cos \theta = \gamma_{SV} - \gamma_{SL}$$

where $\gamma_{LV}$, $\gamma_{SV}$ and $\gamma_{SL}$ refer to the interfacial energies of the liquid/vapor, solid/vapor and solid/liquid interfaces, respectively. If the contact angle θ is less than 90 degrees the liquid is said to wet the solid. If the contact angle is greater than 90 degrees the liquid is non-wetting. A zero contact angle θ represents complete wetting. Thus, preferably the contact angle is less than 90 degrees.

The bipolar devices disclosed herein are particularly useful as non-coaptive tissue sealers in providing hemostasis during surgery. In other words, grasping of the tissue is not necessary to shrink, coagulate and seal tissue against blood loss, for example, by shrinking collagen and associated lumens of blood vessels (e.g., arteries, veins), thereby inhibiting blood flow therethrough and therefrom, to provided the desired hemostasis of the tissue. More particularly, the devices may be useful to shrink blood vessels, either severed or unsevered, during spine surgery, such as blood vessels of the vertebral venous and/or arterial systems during, for example, a discectomy.

Intervertebral discs are flexible pads of fibrocartilaginous tissue tightly fixed between the vertebrae of the spine. The discs comprise a flat, circular capsule roughly an inch in diameter and about 0.25 inch thick, made of a tough, fibrous outer membrane called the annulus fibrosus, surrounding an elastic core called the nucleus pulposus.

Under stress, it is possible for the nucleus pulposus to swell and herniate, pushing through a weak spot in the annulus fibrosus membrane of the disc and into the spinal canal. Consequently, all or part of the nucleus pulposus material may protrude through the weak spot, causing pressure against surrounding nerves which results in pain and immobility.

Where a damaged intervertebral disc must be removed from the patient as part of a discectomy and subsequent fusion of vertebral bodies of the superior and inferior vertebrae, the devices of the present invention may be particularly useful to shrink and seal blood vessels of the vertebral venous and/or arterial systems.

The vertebral venous system includes any of four interconnected venous networks surrounding the vertebral column. These are known as the anterior external vertebral venous plexus (the system around the vertebral bodies), the posterior external vertebral venous plexus (the system around the vertebral processes), the anterior internal vertebral (epidural) venous plexus (the system running the length of the vertebral canal anterior to the dura) and the posterior internal vertebral (epidural) venous plexus (the system running the length of the vertebral canal posterior to the dura), with the latter two constituting the epidural venous plexus. The veins of the exterior vertebral venous plexus communicate with the veins of the interior vertebral venous plexus through intervertebral veins and anterior and posterior segmental medullary/radicular veins of each vertebral level.

The vertebral arterial system includes the segmental arteries of the vertebral column which supply anterior and posterior radicular arteries of the various vertebral levels. In thoracic and lumbar regions, segmental arteries include the posterior intercostal, subcostal and lumbar arteries, which arise from posterior aspect of the aorta. The blood supply to the spinal column is derived from the segmental arteries, which supply two networks: one feeds the bony elements of the vertebrae, the paraspinal muscles, and the extradural space; and the other, an inner network, nourishes the spinal cord itself.

Extending from the aorta, the segmental arteries hug the perimeter of the vertebral bodies of the vertebrae, giving off paravertebral anastomoses, prevertebral anastomoses and a main dorsal branch as they approach the neural foramina. This main dorsal branch continues posteriorly below the transverse process of the vertebrae, supplying the bone of the posterior elements of the vertebrae and the paraspinal muscles. Shortly after its origin, the dorsal branch gives off a spinal branch, which supplies the anterior radicular artery and anterior segmental medullary artery, which ultimately supplies the anterior spinal artery. The spinal branch also supplies a branch to the vertebral body and dura mater, and the posterior radicular artery which ultimately supplies the posterior spinal arteries.

During a posterior discectomy, the devices of the present invention may be more particularly used by a surgeon to seal veins of the posterior external vertebral venous plexus, posterior internal vertebral (epidural) venous plexus and anterior internal vertebral (epidural) venous plexus prior to entering the intervertebral disc space. Alternatively, during an anterior discectomy, the devices of the present invention may be more particularly used by a surgeon to seal veins of the anterior external vertebral venous plexus and segmental arteries, particularly the anterior and lateral-anterior portions adjacent the vertebral bodies.

During a discectomy blood vessels are often cut, ruptured or otherwise severed. These blood vessels bleed, and the resulting blood can flow into the tissue treatment site making visibility more difficult and prolonging the procedure. A method of the present invention may be used to seal such vertebral blood vessels against blood loss before the vessels are cut, rupture or are otherwise severed. This method involves pressing a portion of the blood vessel against a supporting spine structure with a surgical device, such as the devices of the present invention, to provide a compressed portion of the blood vessel, and heating the compressed portion of the blood vessel with the surgical device sufficiently to occlude the blood vessel (e.g. by shrinking the vessel and the lumen by shrinkage of the collagen in the vessel and/or welding the opposite internal surfaces of the lumen together by collagen welding) to inhibit a blood flow through the vessel after the surgical device is removed from the blood vessel.

The supporting spine structure against which the blood vessel is compressed comprises one or more vertebra of the spine, and may further comprise the vertebral body of the vertebra. The vertebra may comprise one of the cervical vertebrae, thoracic vertebrae, or lumbar vertebrae. In addition to the vertebrae, the support structure may also comprise a spinal ligament, such as the anterior longitudinal ligament or the posterior longitudinal ligament, or an intervertebral disc.

Depending on the type of procedure, the supporting spine structure may further comprise an anterior side of the vertebral body of the vertebra or a lateral-anterior side of the vertebral body of the vertebra, which would be encountered during an anterior approach. For a posterior approach, the supporting spine structure may further comprise a posterior side of the vertebral body of the vertebra or a lateral-posterior side of the vertebral body of the vertebrae. The anterior or posterior approach may be part of an endoscopic spine surgery, laparoscopic spine surgery or open spine surgery.

Due to the rigidity of the vertebra and stability of the vertebrae, the blood vessel may be pressed against the vertebra without the vertebra deforming. In this manner, the blood vessel may be compressed, at which time the compressed portion of the vessel may be heated sufficiently to occlude the blood vessel after the surgical device is removed from the blood vessel.

Figure 17:
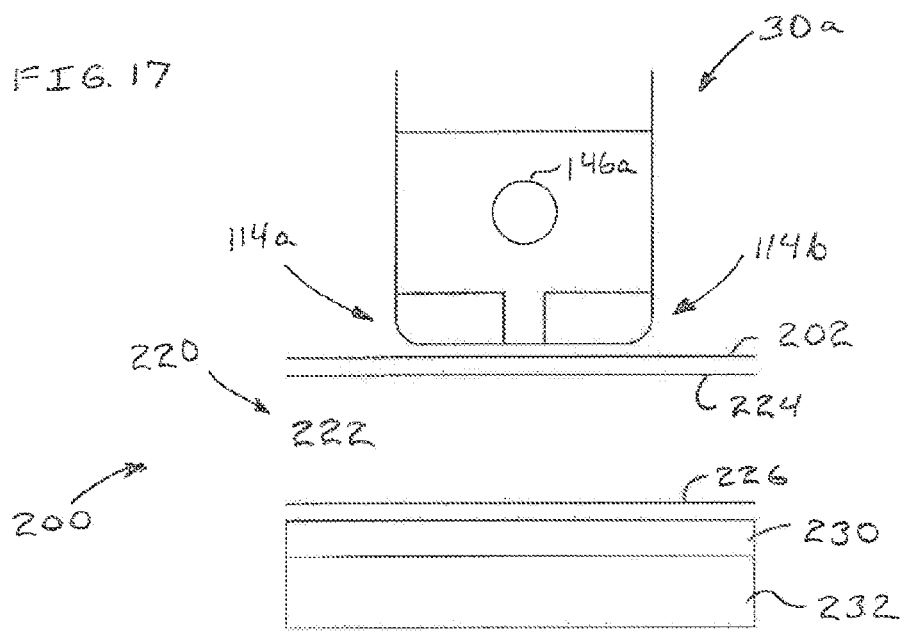
FIG. 17 is a close-up view of a distal portion of the device of FIG. 7 and tissue.

FIG. 17 shows how the distal portion 106 of device 30a (and similarly for devices 30b-30d) may be oriented for use, with the longitudinal axis of shaft 102 vertically oriented and the distal end of device 30a facing a tissue treatment site. In other embodiments, device 30a may be used with the longitudinal axis of shaft 102 horizontally oriented, or at any orientation between vertical and horizontal.

FIG. 17 shows device 30a and tissue 200 prior to treatment thereof. As shown, tissue 200 comprises a blood vessel 220 and more specifically, an epidural vein. Underlying blood vessel 220 is a ligament 230 and, more specifically, a longitudinal ligament of the spine. Underlying ligament 230 is a vertebra 232 and more specifically, a vertebral body of the vertebra 232.

Figure 18:
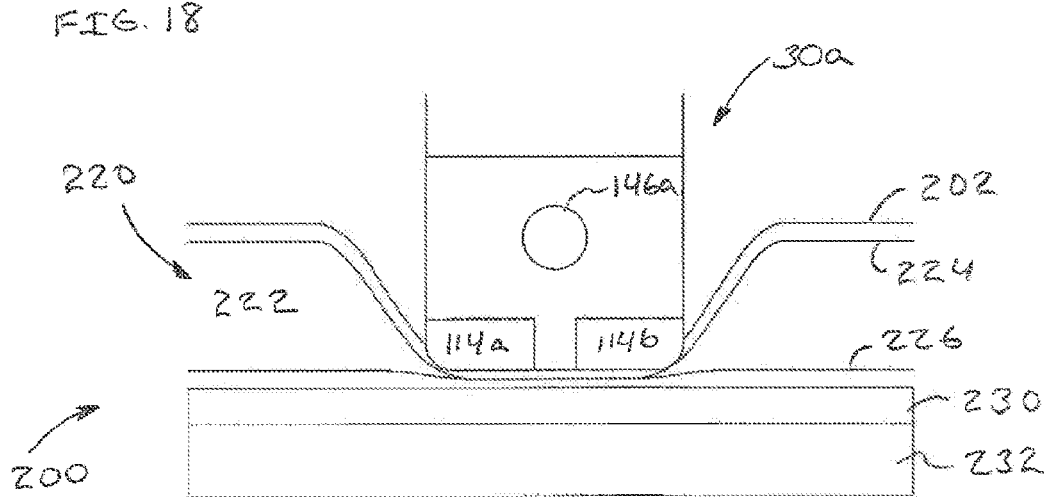
FIG. 18 is a close-up view of a distal portion of the device of FIG. 7 pressing against tissue.

FIG. 18 shows device 30a applied to tissue 200 with sufficient force and pressure applied to device 30a by the user thereof to press a portion of the blood vessel 220 against the supporting spine structure, here ligament 230 and vertebra 232, to provide a compressed portion of the blood vessel 220. In certain embodiments, device 30a may include a feedback mechanism, such as a force or pressure gauge, which alerts the user of the device when sufficient force/pressure is applied to vessel 220. In other embodiments, the feedback mechanism may comprise a light which activates. As shown, electrodes 114a, 114b of device 30a are spaced adjacent tissue surface 202 of tissue 200 by the width of distal spacer portion 126 of housing inner portion 116.

Figure 19:
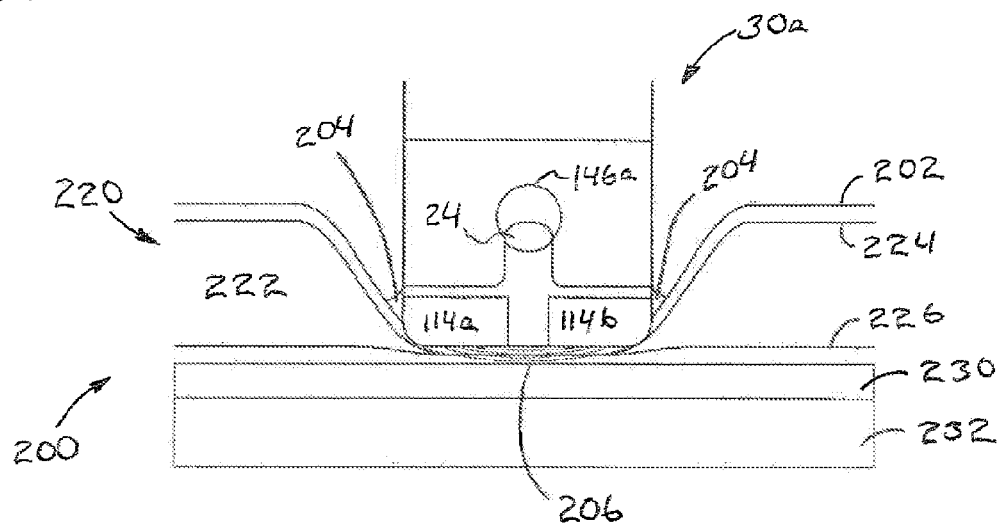
FIG. 19 is a close-up view of a distal portion of the device of FIG. 7 being used to treat tissue.

FIG. 19 shows device 30a in use with fluid 24 expelled from holes 146a, 146b that flows distally to electrodes 114a, 114b to provide a localized fluid coupling 204 between surface 202 of tissue 200 and electrodes 114a, 114b. Preferably fluid 24 couples between the electrodes 114a, 114b and the tissue 200 at both the perimeter 151a, 151b of electrodes 114a, 114b and flat semi-circular shaped electrode portions 138a, 138b of the electrodes 114a, 114b located at the distal end of device 30a. At the same time, RF electrical energy/power, shown by electrical field lines 206, is provided to tissue 200 at tissue surface 202 and below tissue surface 202 into tissue 200 through fluid 24.

Electrodes 114a, 114b are connected to electrosurgical unit 14 to provide RE energy/power and form an alternating current electrical field in tissue 200. In the presence of alternating current, the electrodes 114a, 114b alternate polarity between positive and negative charges with current flow from the positive to negative charge. Without being bound to a particular theory, heating of the tissue is performed by electrical resistance heating. That is, the temperature of the tissue increases as a result of electric current flow through the tissue, with the electrical energy being absorbed from the voltage and transformed into thermal energy (i.e., heat) via accelerated movement of ions as a function of the tissue's electrical resistance.

Heating the compressed portion of blood vessel 220 with device 30a is sufficient to at least partially occlude blood vessel 220 to inhibit blood flow through the vessel 220 after device 30a is removed from vessel 220. Here this is performed by heating vessel 220 sufficiently to shrink the collagen in vessel 220, thereby shrinking the vessel 220 and the lumen 222 of vessel 220. This is also performed by apply sufficient heating and pressure to the compressed portion of vessel 220 to weld the opposing internal surfaces 224 and 226 of the lumen 222 together, here by collagen welding.

The time to shrink tissue containing Type I collagen, such as blood vessels, is generally dependent on temperature. For example, Type I collagen shrinks at an exposure time of about 0.01 seconds when exposed to a temperature of about 85° C., at an exposure time of about 1 second when exposed to a temperature of about 75° C., at an exposure time of about 10 second when exposed to a temperature of about 70° C. and at an exposure time of about 15 minutes when exposed to a temperature of about 65° C. An exemplary target temperature/time for tissue heating is about 75° C. with second. Stated another way, for expediency, the tissue should be heated sufficiently to shrink the collagen in the range between and including about 1 second to 10 seconds after RF activation.

Fluid 24, in addition to providing an electrical coupling between the device 30*a* and tissue 200, cools and lubricates surface 202 of tissue 200 to inhibit electrodes 114*a*, 114*b* from sticking to tissue 200. Depending on the amount of fluid at the distal end of device 30*a* and the tissue treatment site, the fluid coupling 204 may comprise a single coupling which encompasses the distal end of the device 30*a* or a plurality of discrete couplings which are located on each side of the device closest to holes 146*a*, 146*b*.

The fluid coupling for device 30*a* may also comprise a conductive fluid bridge between electrodes 114*a*, 114*b* which rests on surface 202 of tissue 200 and forms a shunt between electrodes 114*a*, 114*b*. Given this scenario, a certain amount of RF energy may be diverted from going into tissue 200 and actually pass between electrodes 114*a*, 114*b* via the conductive fluid bridge. This loss of RF energy may slow down the process of treating the tissue. However, for device 30*a*, having this coupling located between the opposing corners 148*a* and 148*b* and/or opposing corners 149*a* and 149*b* of electrodes 114*a*, 114*b*, respectively, may be desirable as the tissue adjacent to these corners may heat faster or get hotter than other tissue being treated due to the electrode configuration. In such a case, having the fluid coupling 204 at these locations may provide for more balanced heating and treating of tissue 200. Consequently, it may be desirable to provide fluid 24 from device 30*a* in such a quantity that a small portion of the fluid boils to dissipate heat from the tissue while at the same time the fluid diverts a certain amount of RF energy from going into tissue 200 at locations which may heat faster or get hotter than other tissue being treated.

Figure 20:
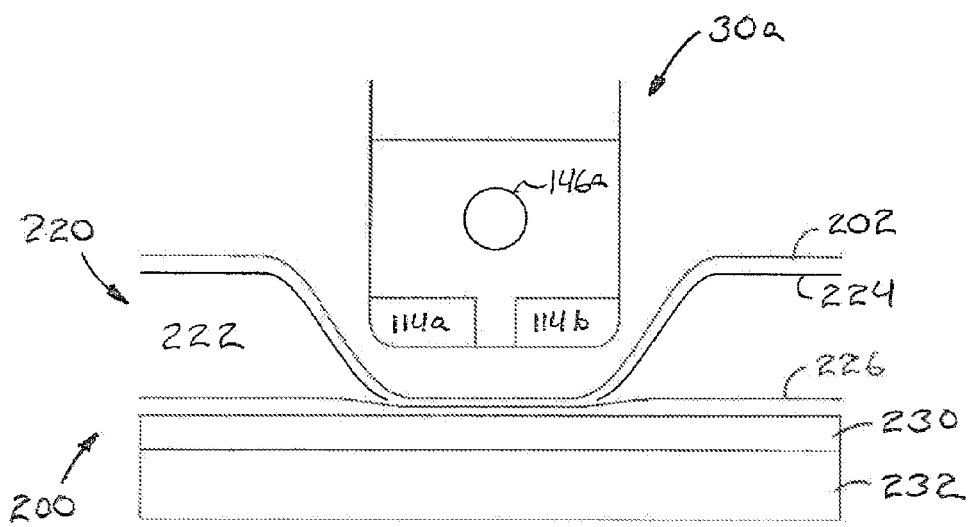
FIG. 20 is a close-up view of a distal portion of the device of FIG. 7 removed from treated tissue.

FIG. 20 shows device 30*a* removed from tissue 200 with the blood vessel 220 sealed against blood loss and blood flow there through.

As established above, the bipolar devices of the present invention inhibit such undesirable effects of tissue desiccation, electrode sticking, char formation and smoke generation, and thus do not suffer from the same drawbacks as prior art dry tip electrosurgical devices. The use of the disclosed devices can result in significantly lower blood loss during surgical procedures. Such a reduction in blood loss can reduce or eliminate the need for blood transfusions, and thus the cost and negative clinical consequences associated with blood transfusions, such as prolonged hospitalization.

While a preferred embodiment of the present invention has been described, it should be understood that various changes, adaptations and modifications can be made therein without departing from the spirit of the invention and the scope of the appended claims. The scope of the invention should, therefore, be determined not with reference to the above description, but instead should be determined with reference to the appended claims along with their full scope of equivalents. Furthermore, it should be understood that the appended claims do not necessarily comprise the broadest scope of the invention which the Applicant is entitled to claim, or the only manner(s) in which the invention may be claimed, or that all recited features are necessary.

All publications and patent documents cited in this application are incorporated by reference in their entirety for all purposes to the extent they are consistent.

What is claimed is:

1. A method of treating tissue having a blood vessel during spine surgery, the method comprising:
providing an electrically powered surgical device having a planar distal end;
pressing a portion of the blood vessel against a supporting spine structure with the planar distal end of the device to provide a compressed portion of the blood vessel; and
heating the compressed portion of the blood vessel with the surgical device sufficiently to occlude the blood vessel after the electrically powered surgical device is removed from the blood vessel.

2. The method according to claim 1 wherein:
the electrically powered surgical device comprises an electrosurgical device.

3. The method according to claim 2 wherein:
the electrosurgical device comprises a bipolar electrosurgical device.

4. The method according to claim 3 wherein:
the bipolar electrosurgical device is configured to treat tissue in a presence of radio frequency power and a fluid provided simultaneously from a distal portion of the device.

5. The method according to claim 1 further comprising:
heating the compressed portion of the blood vessel in a range of at least about 65° Celsius to about 85° Celsius.

6. The method according to claim 1 further comprising:
heating the compressed portion of the blood vessel in a range of at least about 7° Celsius to about 75° Celsius.

7. The method according to claim 1 further comprising:
heating the compressed portion of the blood vessel in a range of about 70° Celsius to about 100° Celsius.

8. The method according to claim 1 wherein:
the supporting spine structure comprises a vertebra.

9. The method according to claim 8 wherein:
the supporting spine structure further comprises a vertebral body of the vertebra.

10. The method according to claim 9 wherein:
the supporting spine structure further comprises an anterior side of the vertebral body of the vertebra.

11. The method according to claim 9 wherein:
the supporting spine structure further comprises a lateral-anterior side of the vertebral body of the vertebra.

12. The method according to claim 9 wherein:
the supporting spine structure further comprises a posterior side of the vertebral body of the vertebra.

13. The method according to claim 9 wherein:
the supporting spine structure further comprises a lateral-posterior side of the vertebral body of the vertebra.

14. The method according to claim 1 wherein:
the supporting spine structure comprises a spinal ligament and a vertebra.

15. The method according to claim 1 wherein:
the spine surgery further comprises a discectomy.

16. The method according to claim 1 wherein:
the spine surgery further comprises a spinal fusion.

* * * * *